(12) United States Patent
Luepke et al.

(10) Patent No.: US 11,370,211 B2
(45) Date of Patent: Jun. 28, 2022

(54) METHOD OF MAKING A LAMINATE

(71) Applicant: 3M INNOVATIVE PROPERTIES COMPANY, St. Paul, MN (US)

(72) Inventors: Ryan M. Luepke, Eagan, MN (US); Scott M. Niemi, St. Paul, MN (US); Thomas J. Gilbert, St. Paul, MN (US); Adam A. Krzmarzick, Hector, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 17/049,160

(22) PCT Filed: Apr. 25, 2019

(86) PCT No.: PCT/IB2019/053427
§ 371 (c)(1),
(2) Date: Oct. 20, 2020

(87) PCT Pub. No.: WO2019/207529
PCT Pub. Date: Oct. 31, 2019

(65) Prior Publication Data
US 2021/0237421 A1 Aug. 5, 2021

Related U.S. Application Data

(60) Provisional application No. 62/662,538, filed on Apr. 25, 2018.

(51) Int. Cl.
*B32B 37/00* (2006.01)
*A44B 18/00* (2006.01)
(Continued)

(52) U.S. Cl.
CPC ........ *B32B 37/203* (2013.01); *A44B 18/0069* (2013.01); *A61F 13/15699* (2013.01);
(Continued)

(58) Field of Classification Search
CPC . Y10T 156/1077; B32B 37/203; B32B 5/022; B32B 7/12; B32B 27/12;
(Continued)

(56) References Cited

U.S. PATENT DOCUMENTS 3,192,927 A 7/1965 Chauviere
3,645,433 A 2/1972 Lucas
(Continued)

FOREIGN PATENT DOCUMENTS

EP 0233704 8/1987
EP 1066008 B1 3/2004
(Continued)

OTHER PUBLICATIONS

International Search Report for PCT International Application No. PCT/IB2019/053427, dated Jul. 12, 2019, 4 pages.

*Primary Examiner* — Linda L Gray
(74) *Attorney, Agent, or Firm* — Kathleen B. Gross

(57) ABSTRACT

The method includes providing a thermoplastic web having mechanical fastening elements and a nonlinear line of weakness that extends predominantly in a first direction and demarcates nonlinear edges of two sub-webs but does not sever the thermoplastic web. The method further includes severing the thermoplastic web at the nonlinear line of weakness into the two sub-webs and joining the two sub-webs to a carrier to form the laminate. The two sub-webs are separated in a second direction perpendicular to the first direction. Severing the thermoplastic web and joining the two sub-webs to the carrier are carried out in-line without offsetting the two sub-webs in the first direction.

20 Claims, 6 Drawing Sheets

(51) Int. Cl.

| | | |
|---|---|---|
| *A61F 13/00* | (2006.01) | |
| *B32B 5/00* | (2006.01) | |
| *B32B 7/00* | (2019.01) | |
| *B32B 27/00* | (2006.01) | |
| *B32B 38/00* | (2006.01) | |
| *B32B 37/20* | (2006.01) | |
| *A61F 13/15* | (2006.01) | |
| *B32B 5/02* | (2006.01) | |
| *B32B 7/12* | (2006.01) | |
| *B32B 27/12* | (2006.01) | |
| *B32B 37/06* | (2006.01) | |
| *B32B 37/12* | (2006.01) | |
| *B32B 38/04* | (2006.01) | |

(52) U.S. Cl.
CPC ........ *A61F 13/15756* (2013.01); *B32B 5/022* (2013.01); *B32B 7/12* (2013.01); *B32B 27/12* (2013.01); *B32B 37/06* (2013.01); *B32B 37/12* (2013.01); *B32B 38/0004* (2013.01); *B32B 38/04* (2013.01); *B32B 2038/045* (2013.01); *B32B 2555/02* (2013.01)

(58) Field of Classification Search
CPC ..... B32B 37/06; B32B 37/12; B32B 38/0004; B32B 38/04; B32B 2038/045; B32B 2555/02; A44B 18/0069; A61F 13/15699; A61F 13/15756
See application file for complete search history.

(56) References Cited

U.S. PATENT DOCUMENTS

| | | | |
|---|---|---|---|
| 3,713,190 A | 1/1973 | Yazawa | |
| 3,724,737 A | 4/1973 | Bodnar | |
| 3,985,599 A | 10/1976 | Lepoutre | |
| 3,985,600 A | 10/1976 | Blais | |
| 4,001,366 A | 1/1977 | Brumlik | |
| 4,176,775 A | 12/1979 | Brendemuehl | |
| 4,239,141 A | 12/1980 | Frye | |
| 4,670,960 A | 6/1987 | Provost | |
| 4,775,310 A | 10/1988 | Fischer | |
| 4,842,794 A | 6/1989 | Hovis | |
| 4,862,565 A | 9/1989 | Damour | |
| 4,925,080 A | 5/1990 | Crouse | |
| 4,938,753 A * | 7/1990 | Van Gompel | A61F 13/49015 604/385.29 |
| 4,969,970 A | 11/1990 | Suzuki | |
| 5,043,036 A | 8/1991 | Swenson | |
| 5,077,870 A | 1/1992 | Melbye | |
| 5,207,962 A | 5/1993 | Hovis | |
| 5,256,231 A | 10/1993 | Gorman | |
| 5,290,377 A | 3/1994 | Aihara | |
| 5,399,219 A | 3/1995 | Roessler | |
| 5,517,737 A | 5/1996 | Viltro | |
| 5,560,793 A | 10/1996 | Ruscher | |
| 5,580,411 A * | 12/1996 | Nease | A61F 13/49009 156/260 |
| 5,605,729 A | 2/1997 | Mody | |
| 5,628,097 A | 5/1997 | Benson | |
| 5,660,666 A | 8/1997 | Dilnik | |
| 5,692,271 A | 12/1997 | Provost | |
| 5,705,013 A | 1/1998 | Nease | |
| 5,729,878 A | 3/1998 | Kurihara | |
| 5,759,317 A | 6/1998 | Justmann | |
| 5,791,030 A | 8/1998 | Aihara | |
| 5,953,797 A | 9/1999 | Provost | |
| 6,132,660 A | 10/2000 | Kampfer | |
| 6,190,594 B1 | 2/2001 | Gorman | |
| 6,287,665 B1 | 9/2001 | Hammer | |
| 6,481,063 B2 | 11/2002 | Shepard | |
| 6,489,003 B1 | 12/2002 | Levitt | |
| 6,627,133 B1 | 9/2003 | Tuma | |
| 6,743,324 B2 * | 6/2004 | Hargett | A61F 13/15699 156/259 |
| 6,843,762 B2 | 1/2005 | Munche | |
| 6,973,702 B2 | 12/2005 | Harashige | |
| 7,001,475 B2 | 2/2006 | Ausen | |
| 7,014,906 B2 | 3/2006 | Tuman | |
| 7,048,818 B2 | 5/2006 | Krantz | |
| 7,125,400 B2 | 10/2006 | Igaue | |
| 7,198,743 B2 | 4/2007 | Tuma | |
| 7,214,334 B2 | 5/2007 | Jens | |
| 7,219,403 B2 | 5/2007 | Miyamoto | |
| 7,223,314 B2 | 5/2007 | Provost | |
| 7,241,483 B2 | 7/2007 | Ausen | |
| 7,252,730 B2 | 8/2007 | Hoffman | |
| 7,371,302 B2 | 5/2008 | Miyamoto | |
| 7,407,496 B2 | 8/2008 | Peterson | |
| 7,517,572 B2 | 4/2009 | Van Dyke | |
| 7,622,180 B2 | 11/2009 | Seth | |
| 7,658,813 B2 | 2/2010 | Petersen | |
| 7,855,316 B2 | 12/2010 | Meyer | |
| 8,020,262 B2 | 9/2011 | Oertel | |
| 8,777,919 B2 | 7/2014 | Kimura | |
| 8,956,496 B2 | 2/2015 | Biegler | |
| 9,096,960 B2 | 8/2015 | Biegler | |
| 9,126,224 B2 | 9/2015 | Biegler | |
| 9,138,031 B2 | 9/2015 | Wood | |
| 9,138,957 B2 | 9/2015 | Wood | |
| 9,314,962 B2 | 4/2016 | Rothwell | |
| 9,591,896 B2 | 3/2017 | Gilbert | |
| 9,630,359 B2 | 4/2017 | Rothwell | |
| 9,649,824 B2 | 5/2017 | Chandrasekaran | |
| 9,687,048 B2 | 6/2017 | Gilbert | |
| 10,967,624 B2 | 4/2021 | Gilbert | |
| 10,973,710 B2 | 4/2021 | Peltier | |
| 2003/0008106 A1 | 1/2003 | Guenther | |
| 2003/0130644 A1 | 7/2003 | Baker | |
| 2004/0147890 A1 | 7/2004 | Nakahata | |
| 2004/0209042 A1 | 10/2004 | Peacock | |
| 2004/0261230 A1 | 12/2004 | Neeb | |
| 2004/0261232 A1 | 12/2004 | Kurtz, Jr. | |
| 2005/0123720 A1 | 6/2005 | Suzuki | |
| 2006/0293635 A1 | 12/2006 | Petersen | |
| 2007/0039142 A1 | 2/2007 | Petersen | |
| 2007/0107571 A1 | 5/2007 | Saeki | |
| 2007/0134489 A1 | 6/2007 | Neugebauer | |
| 2009/0311465 A1 | 12/2009 | De Jong | |
| 2011/0151171 A1 | 6/2011 | Biegler | |
| 2012/0086145 A1 | 4/2012 | Nakamura | |
| 2012/0204383 A1 | 8/2012 | Wood | |
| 2012/0330266 A1 | 12/2012 | Zonneveld | |
| 2014/0114272 A1 | 4/2014 | Schoon | |
| 2014/0142533 A1 | 5/2014 | Peltier | |
| 2016/0106595 A1 | 4/2016 | Arbesman | |

FOREIGN PATENT DOCUMENTS

| | | |
|---|---|---|
| JP | 2010-29532 | 2/2010 |
| WO | WO 1994-002091 | 2/1994 |
| WO | WO 1996-010481 | 4/1996 |
| WO | WO 2005-122818 | 12/2005 |
| WO | WO 2011-163020 | 12/2011 |
| WO | WO 2014-201219 | 12/2014 |
| WO | WO 2015-066210 | 5/2015 |
| WO | WO 2017-112603 | 6/2017 |

\* cited by examiner

METHOD OF MAKING A LAMINATE

CROSS-REFERENCE TO RELATED APPLICATION

This application is a national stage filing under 35 U.S.C. 371 of PCT/IB2019/053427, filed Apr. 25, 2019, which claims priority to U.S. Provisional Application No. 62/662,538, filed Apr. 25, 2018, the disclosure of which is incorporated by reference in its entirety herein.

BACKGROUND

Slitting films during a continuous web process can be useful for providing multiple smaller films of a desired size. In some applications it is desirable to use multiple strips of a film in a single product or to use an apertured film to enhance some performance aspect of the product.

Some mechanical fastening laminates have been made with openings in the backing from which male fastening elements project. See, e.g., U.S. Pat. No. 4,001,366 (Brumlik), U.S. Pat. No. 7,407,496 (Peterson), and U.S. Pat. No. 9,138,031 (Wood et al.) and Int. Pat. Appl. Pub. Nos. WO 2005/122818 (Ausen et al.) and WO 1994/02091 (Hamilton). In U.S. Pat. No. 7,407,496 (Peterson), a method of making such a laminate is disclosed in which a continuous backing bearing a plurality of male fastening elements is provided with one or 2n+1 continuous cuts having a periodic sequence of notches and protrusions in the machine direction to form two or 2n adjacent sub-backings. The sub-backings are then separated from each other in both the cross-direction and the machine direction.

Also, laminates with separated mechanical fastening strips are described in U.S. Pat. Appl. Pub. No. 2007/0039142 (Petersen et al.) and Int. Pat. Appl. Pub. No. WO2011/163020 (Hauschildt et al.).

Some nonwoven materials have been made with openings Such nonwovens have been attached to elastics or extensible pleated backings. See, e.g., U.S. Pat. Appl. Pub. No. 2004/0147890 (Nakahata et al.), Int. Pat. Appl. Pub. No. WO 1996/10481 (Abuto et al.), and European Patent No. EP 1066008 B1 (Eaton et al.). A reticulated mechanical fastening patch having loops is described in U.S. Pat. Appl. Pub. No. 2012/0330266 (Zonneveld et al.).

SUMMARY

When making a mechanical fastening laminate having strips of mechanical fastener with nonlinear edges, it is difficult to keep the strips in registration with each other. The present disclosure provides a method of making a laminate. The laminate includes at least two strips of a thermoplastic web on a carrier. Each of the strips has at least one nonlinear edge. The method includes severing the thermoplastic web and joining the strips to the carrier. The severing and joining are carried out in-line without offsetting the nonlinear edges of the at least two strips.

In one aspect, the present disclosure provides a method of making a laminate. The method includes providing a thermoplastic web having mechanical fastening elements and a nonlinear line of weakness that extends predominantly in a first direction and demarcates nonlinear edges of two sub-webs but does not sever the thermoplastic web. The method further includes severing the thermoplastic web at the nonlinear line of weakness into the two sub-webs and joining the two sub-webs to a carrier to form the laminate. The two sub-webs are separated in a second direction perpendicular to the first direction. Severing the thermoplastic web and joining the two sub-webs to the carrier are carried out in-line without offsetting the two sub-webs in the first direction.

The method according to the present disclosure allows strips of mechanical fastener and, in some embodiments, openings in the mechanical fastener to be provided without wasteful material loss. The amount of separation between the sub-webs or between the strands in the sub-webs in the methods disclosed herein may be adjusted based upon, for example, the desired flexibility, breathability, weight, cost, or appearance in the final product.

The method disclosed herein may be useful, for example, for making a mechanical fastening web laminate that has a unique appearance. The spaces between strips and, in some embodiments, openings can provide breathability and flexibility to the mechanical fastener, which may enhance the comfort of the wearer, for example, of an absorbent article comprising the laminate made by the method disclosed herein. With spaces between strips and, in some embodiments, openings, the mechanical fastener also is typically able to cover a relatively large area with a relatively small amount of material, which may lower its cost. Also, because of the large area that may be covered by the mechanical fastener in an absorbent article, the laminate may provide performance enhancement, for example, by resisting shifting forces such as torsional or rotational forces caused by movement of the wearer of the absorbent article. For example, in use, fitting an absorbent article such as a diaper about the wearer usually requires the front and back waist portions of the diaper to overlap each other. As the diaper is worn the movements of the wearer tend to cause the overlapping front and back waist portions to shift position relative to each other. Unless such shifting is limited, the fit and containment characteristics of the diaper may be degraded as the diaper is worn. The laminate made according to the present disclosure may provide improved fit and closure stability by resisting such shifting because of its relatively larger area and flexibility.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

The terms "first" and "second" are used in this disclosure. It will be understood that, unless otherwise noted, those terms are used in their relative sense only. For these components, the designation of "first" and "second" may be applied to the components merely as a matter of convenience in the description of one or more of the embodiments.

The term "low-friction surface" refers to a surface made from any material or coated with any material that allows slit web to slip over the crown surface to at least some degree. The "low-friction surface" typically has a low coefficient of friction relative to the slit web. The coefficient of friction between the "low-friction surface" and the slit web is typically up to 0.2. In some embodiments, "low-friction surface" can mean non-rubber surface.

The term "elastic" refers to any material (such as a film that is 0.002 mm to 0.5 mm thick) that exhibits recovery from stretching or deformation. In some embodiments, a material may be considered to be elastic if, upon application of a stretching force, it can be stretched to a length that is at least about 25 (in some embodiments, 50) percent larger than its initial length and can recover at least 40, 50, 60, 70, 80, or 90 percent of its elongation upon release of the stretching force.

The terms "multiple" and "a plurality" refer to more than one.

The term "opening" should be understood to be a void space in the mechanical fastener material that is surrounded by the mechanical fastener web. One opening is typically enclosed by two of the multiple strands.

The term "in-line," as used herein, means that the steps are completed without the thermoplastic web being rolled up on itself. The steps may be completed sequentially with or without additional steps in-between. For clarification, the thermoplastic web may be supplied in rolled form and the finished laminate may be rolled up on itself. However, the thermoplastic web is not rolled up on itself after the severing step or before the joining step.

The term "web" can refer to a continuous or running web, sometimes having an indefinite length. A web can typically be handled in a roll-to-roll process. The term "machine direction" (MD) as used above and below denotes the direction of a running web of material during the manufacturing of the mechanical fastener. When a mechanical fastening strip is cut from a continuous web, the machine direction corresponds to the length "L" of the mechanical fastening strip. As used herein, the terms "machine direction" and "longitudinal direction" are typically used interchangeably. The term "cross-machine direction" (CD) as used above and below denotes the direction which is essentially perpendicular to the machine direction. When a mechanical fastening strip is cut from a continuous web, the cross-machine direction corresponds to the width "W" of the mechanical fastening strip.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which.

DETAILED DESCRIPTION

Figure 1:
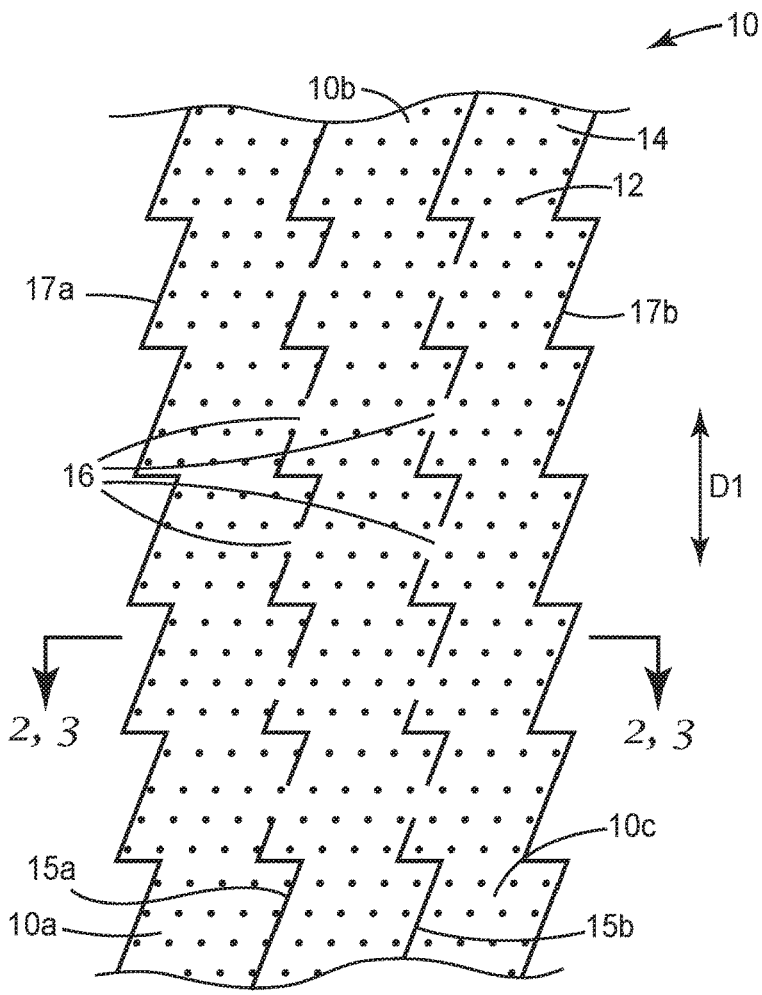
FIG. 1 is a top view of an embodiment of a portion of a web useful for the method of making a laminate disclosed herein, in which the web has two nonlinear lines of weakness.

Reference will now be made in detail to embodiments of the disclosure, one or more examples of which are illustrated in the drawings. Features illustrated or described as part of one embodiment can be used with other embodiments to yield still a third embodiment. It is intended that the present disclosure include these and other modifications and variations.

Suitable thermoplastic materials for the thermoplastic webs useful for practicing the present disclosure include polyolefin homopolymers such as polyethylene and polypropylene, copolymers of ethylene, propylene and/or butylene; copolymers containing ethylene such as ethylene vinyl acetate and ethylene acrylic acid; polyesters such as poly(ethylene terephthalate), polyethylene butyrate and polyethylene napthalate; polyamides such as poly(hexamethylene adipamide); polyurethanes; polycarbonates; poly(vinyl alcohol); ketones such as polyetheretherketone; polyphenylene sulfide; and mixtures thereof. Typically, the thermoplastic is a polyolefin (e.g., polyethylene, polypropylene, polybutylene, ethylene copolymers, propylene copolymers, butylene copolymers, and copolymers and blends of these materials).

In the embodiments of the thermoplastic web useful in the methods disclosed herein that include male fastening elements, the backing and the male fastening elements are typically integral (that is, formed at the same time as a unit, unitary). Upstanding posts on a backing can be made, for example, by feeding a thermoplastic material onto a continuously moving mold surface with cavities having the inverse shape of the posts. The thermoplastic material can be passed between a nip formed by two rolls or a nip between a die face and roll surface, with at least one of the rolls having the cavities. The cavities may be in the inverse shape of a capped post having a loop-engaging head or may be in the inverse shape of an upstanding post without loop-engaging heads (e.g., a precursor to a male fastening element). Pressure provided by the nip forces the resin into the cavities. In some embodiments, a vacuum can be used to evacuate the cavities for easier filling of the cavities. The nip typically has a large enough gap such that a coherent backing is formed over the cavities. The mold surface and cavities can optionally be air or water cooled before stripping the integrally formed backing and upstanding hook elements from the mold surface such as by a stripper roll. If the posts formed upon exiting the cavities do not have loop-engaging heads, loop-engaging heads could be subsequently formed into hooks by a capping method as described in U.S. Pat. No. 5,077,870 (Melbye et al.). Typically, the capping method includes deforming the tip portions of the hook elements using heat and/or pressure. The heat and pressure, if both are used, could be applied sequentially or simultaneously.

Suitable tool rolls include those formed from a series of plates defining a plurality of post-forming cavities about its periphery such as those described, for example, in U.S. Pat. No. 4,775,310 (Fischer). Cavities may be formed in the plates by drilling or photoresist technology, for example. Other suitable tool rolls may include wire-wrapped rolls, which are disclosed along with their method of manufacturing, for example, in U.S. Pat. No. 6,190,594 (Gorman et al.). Another example of a method for forming a thermoplastic backing with upstanding posts includes using a flexible mold belt defining an array of upstanding post-shaped cavities as described in U.S. Pat. No. 7,214,334 (Jens et al.). Yet other useful methods for forming a thermoplastic backing with upstanding posts can be found in U.S. Pat. No. 6,287,665 (Hammer), U.S. Pat. No. 7,198,743 (Tuma), and U.S. Pat. No. 6,627,133 (Tuma).

The male fastening elements in the thermoplastic web useful for practicing the present disclosure may have loop-engaging heads that have an overhang or may be upstanding posts having distal tips that can be formed into loop-engaging heads, if desired. The term "loop-engaging" as used herein relates to the ability of a male fastening element to be mechanically attached to a loop material. Generally, male fastening elements with loop-engaging heads have a head shape that is different from the shape of the post. For example, the male fastening element may be in the shape of a mushroom (e.g., with a circular or oval head enlarged with respect to the stem), a hook, a palm-tree, a nail, a T, or a J. In some embodiments, each male fastening element has a cap with loop engaging overhangs extending in multiple (i.e., at least two) directions. For example, the upstanding post may be in the shape of a mushroom, a nail, a palm tree, or a T. In some embodiments, the upstanding posts are provided with a mushroom head (e.g., with an oval or round cap distal from the thermoplastic backing). In other embodiments, loop-engaging overhangs (e.g., at the cap or head) on the upstanding posts of the slit web extend parallel to the MD. For example, the upstanding posts may have the shape of a J (e.g., as shown in U.S. Pat. No. 5,953,797 (Provost et al.).

The loop-engageability of male fastening elements may be determined and defined by using standard woven, non-woven, or knit materials. A region of male fastening elements with loop-engaging heads generally will provide, in combination with a loop material, at least one of a higher peel strength, higher dynamic shear strength, or higher dynamic friction than a region of posts without loop-engaging heads. Male fastening elements that have "loop-engaging overhangs" or "loop-engaging heads" do not include ribs that are precursors to fastening elements (e.g., elongate ribs that are profile extruded and subsequently cut to form male fastening elements upon stretching in the direction of the ribs). Such ribs would not be able to engage loops before they are cut and stretched. Such ribs would also not be considered upstanding posts. Typically, male fastening elements that have loop-engaging heads have a maximum thickness dimension (in either dimension normal to the height) of up to about 1 (in some embodiments, 0.9, 0.8, 0.7, 0.6, 0.5, or 0.45) millimeter. In some embodiments, the male fastening elements have a maximum height (above the backing) of up to 3 mm, 1.5 mm, 1 mm, or 0.5 mm and, in some embodiments a minimum height of at least 0.05 mm, 0.1 mm, or 0.2 mm. In some embodiments, the upstanding posts have aspect ratio (that is, a ratio of height to width at the widest point) of at least about 2:1, 3:1, or 4:1.

Loop materials useful for practicing some embodiments of the present disclosure (e.g., when the mechanical fastening elements are loops) can be any suitable material that interlocks with corresponding hook fastening elements. In some embodiments, the loop fastening elements are typically formed from knitted fabrics, woven fabrics, or non-woven fabrics. The term "non-woven" refers to a material having a structure of individual fibers or threads that are interlaid but not in an identifiable manner such as in a knitted fabric. Examples of non-woven webs include spunbond webs, spunlaced webs, airlaid webs, meltblown web, and bonded carded webs. The thermoplastic web useful in the method disclosed herein may include fiber loops projecting from a knitted, woven, or non-woven backing or may be extrusion-bonded, adhesive-bonded, and/or sonically-bonded fiber loops. Useful loop materials may be made of natural fibers (e.g., wood or cotton fibers), synthetic fibers (e.g., thermoplastic fibers), or a combination of natural and synthetic fibers. Examples of suitable materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material.

In some embodiments, the loop material comprises a fibrous layer disposed on a backing. Suitable backings include textiles, paper, thermoplastic films (e.g., single- or multilayered films, coextruded films, laterally laminated films, or films comprising foam layers), and combinations thereof. For thermoplastic backings, the thermoplastic can be any of those described above in connection with a thermoplastic backing having male fastening elements. Examples of suitable loop materials are described, for example, in U.S. Pat. No. 5,256,231 (Gorman et al.) and U.S. Pat. No. 5,389,416 (Mody et al.). As described in U.S. Pat. No. 5,256,231 (Gorman et al.), the fibrous layer in a loop material according to some embodiments disclosed herein comprises arcuate portions projecting in the same direction from spaced anchor portions on the backing.

In embodiments wherein the thermoplastic web either has male fastening elements (e.g., upstanding posts) or a fibrous layer on a backing, the thickness of the backing may be up to about 400, 250, 150, 100, 75 or 50 micrometers, depending on the desired application. In some embodiments, the thickness of the backing is in a range from 30 to about 225 micrometers, from about 50 to about 200 micrometers, or from about 100 to about 150 micrometers. In some embodiments, the thermoplastic web has stretch-induced molecular orientation, for example, when the thermoplastic backing is stretched after formation of upstanding posts. In other embodiments, the thermoplastic web is not provided with macroscopic stretch-induced molecular orientation in the predominant direction of the nonlinear lines of weakness or, in some embodiments, the direction of spreading. In these embodiments, there may be some stress-induced orientation localized in the bridging regions.

Various embodiments of the thermoplastic web useful in the method disclosed herein and laminates made from the thermoplastic web using the method of the present disclosure are illustrated in FIGS. 1 to 10 and described below.

FIG. 1 illustrates an example of a portion of a thermoplastic web 10 with nonlinear lines of weakness 15*a*, 15*b* that is useful for practicing the method disclosed herein. In the illustrated embodiment, the mechanical fastening elements of the thermoplastic web 10 are male fastening elements 12. Illustrated thermoplastic web 10 has a backing 14 with multiple rows of male fastening elements 12 projecting from a first surface of the backing 14. The first surface of the backing is the surface that is visible in FIG. 1. The first surface (that is, the surface with mechanical fastening elements) can also be called the first major surface in any of the embodiments disclosed herein. In the illustrated embodiment, the multiple rows 16 of male fastening elements 12 are aligned in the CD although this is not a requirement. The term "row" refers to male fastening elements lined up in a particular direction. The row or line of male fastening elements may be substantially straight, but this is not a requirement.

Nonlinear lines of weakness 15a, 15b can have a variety of different shapes. In same embodiments, including the embodiment illustrated in FIG. 1, the nonlinear lines of weakness 15a, 15b have a wave shape. The wave may be rectilinear and comprise at least one of a square wave, triangle wave, sawtooth wave, or trapezoidal wave. In the illustrated embodiment, the nonlinear lines of weakness 15a, 15b are in the shape of a sawtooth wave. Typically, when there is more than one nonlinear line of weakness 15a, 15b, they have the same shape, but in some cases multiple nonlinear lines of weakness in a thermoplastic web can have different shapes. Being nonlinear, the lines of weakness change directions but can be said to have a predominant direction. The predominant direction can be understood as the propagation direction of a wave. The nonlinear lines of weakness 15a, 15b extend predominantly in the direction of the running web (the machine direction MD). Thermoplastic web 10 also has two opposing nonlinear longitudinal outer edges 17a, 17b. In other embodiments, at least one of the longitudinal side edges is straight. Nonlinear longitudinal side edges 17a, 17b may have the same or different shape than the nonlinear lines of weakness. In the embodiment illustrated in FIG. 1, each of the nonlinear side edges 17a, 17b and the nonlinear lines of weakness 15a, 15b has the same shape.

Nonlinear line of weakness 15a demarcates nonlinear edges of two sub-webs 10a and 10b, but does not sever the thermoplastic web 10. In some embodiments, the thermoplastic web includes only one nonlinear line of weakness forming only two sub-webs. In other embodiments, including the embodiment illustrated in FIG. 1, there are at least two nonlinear lines of weakness 15a, 15b demarcating nonlinear edges of at least three sub-webs 10a, 10b, 10c of the thermoplastic web without severing the web. The thermoplastic web 10 may include at least three, four, or five and up to nine, 14, 19, or more nonlinear lines of weakness, depending on the desired number of sub-webs in the laminate, A number "n" of nonlinear lines of weakness results in n+1 sub-webs.

Figure 2:
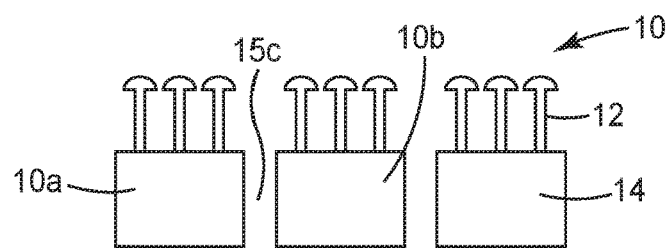
FIG. 2 is an expanded cross-sectional side view of an embodiment of FIG. 1 taken through line 2,3-2,3.

A cross-section taken through thermoplastic web 10 of FIG. 1 at line 2, 3-2, 3, which extends through the nonlinear lines of weakness 15a, 15b, is shown in FIG. 2. In the embodiment shown in FIG. 2, the nonlinear lines of weakness 15c are formed as a series of perforations that extend through the backing 14. The nonlinear lines of weakness 15c are made without removing material from the thermoplastic but are shown out of scale in FIG. 2 to make them more easily visible. In other words, before the thermoplastic web 10 is severed, the two or more sub-webs 10a, 10b on either side of the nonlinear line of weakness 15c are abutting and not spaced apart. Referring again to FIG. 1, when the nonlinear lines of weakness 15a, 15b are in the form of a series of perforations, the thermoplastic web 10 includes connection points 16 where the thermoplastic web 10 is not cut through. The connection points 16 allow the thermoplastic web 10 to be not severed by the nonlinear lines of weakness.

Figure 3:
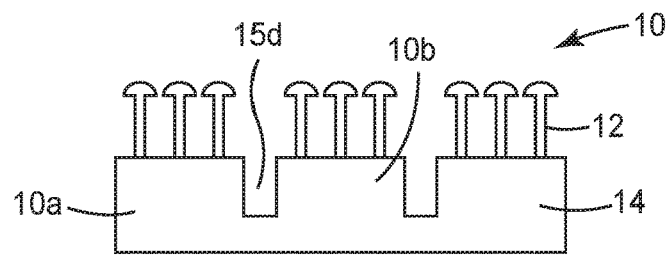
FIG. 3 is an expanded cross-sectional side view of another embodiment of FIG. 1 taken through line 2,3-2,3.

The nonlinear lines of weakness 15a, 15b shown in FIG. 1 can also be formed as partial-depth slits as shown in FIG. 3. In FIG. 3, partial-depth slits 15d are cut into the first face of the backing 14 (i.e., the same face from which the mechanical fastening elements 12 project). In this embodiment, the connection points 16 in the thermoplastic web 10 may or may not be present. In some embodiments, the partial-depth slits 15d penetrate the thickness of the backing 14 in a range from 40 to 90 percent. The partial-depth slit 15d may penetrate, for example, 80, 85, or 90 percent of the thickness of the web or more, which means the solution to the equation:

$$(\text{depth of the slit divided by the thickness of the web}) \times 100$$

is at least 80, 85, or 90 in some embodiments. The depth of the partial-depth slit can be selected based on the method used for severing the thermoplastic web such that partial-depth slit can be severed during the method of the present disclosure. Again, in this embodiment, the partial-depth slits 15d are typically made without removing material from the thermoplastic web 10 but are shown out of scale in FIG. 3 to make them more easily visible.

Figure 4:
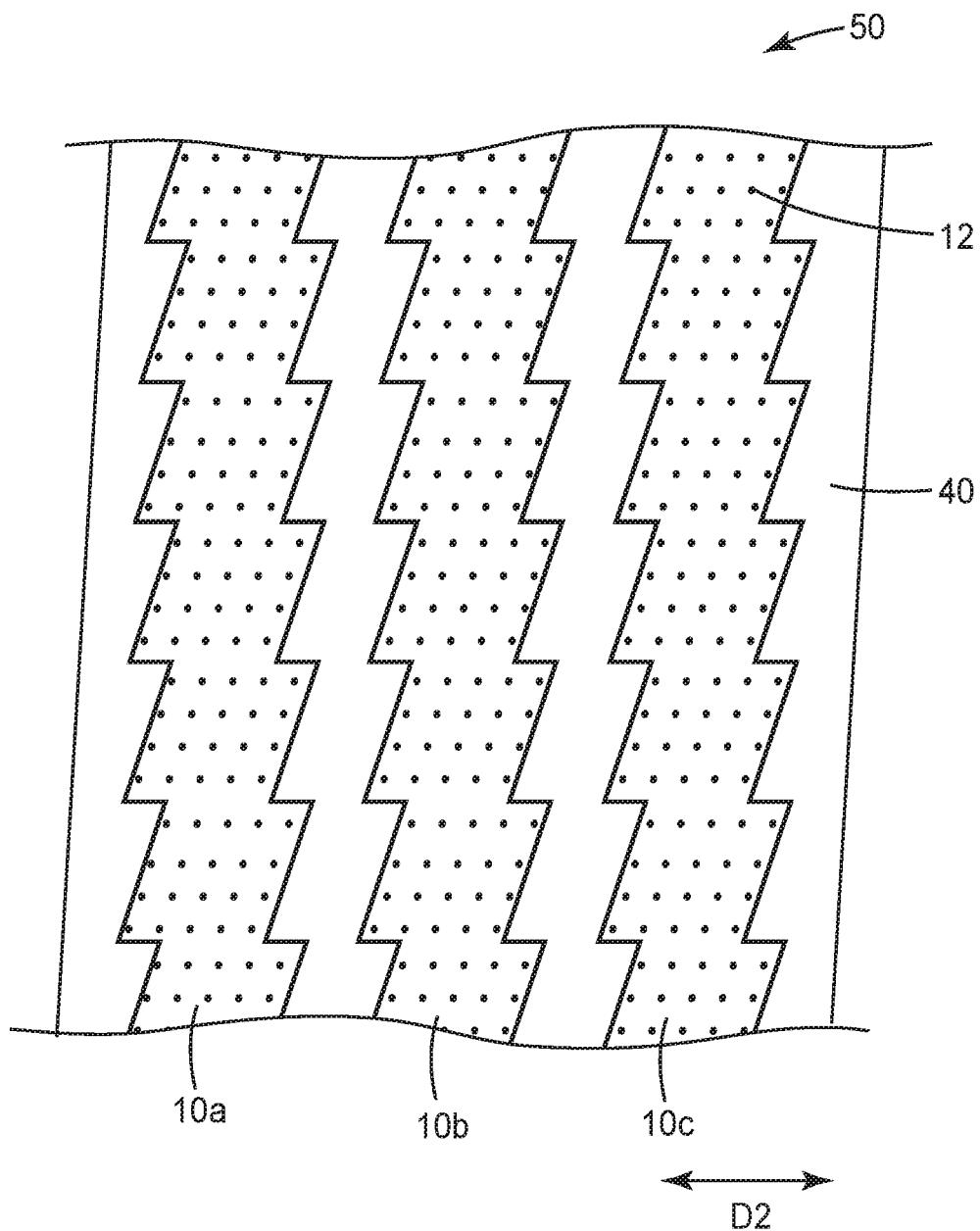
FIG. 4 is a top view of an embodiment of a laminate made from the web of FIG. 1 using an embodiment of the method of the present disclosure.

FIG. 4 illustrates a laminate 50 made from the thermoplastic web shown in FIG. 1 using an embodiment of the method of the present disclosure. After severing the thermoplastic web 10 at the nonlinear lines of weakness 15a, 15b, the sub-webs 10a, 10b, 10c are joined to a carrier 40. The sub-webs 10a, 10b, 10c may be joined to carrier 40, for example, by at least one of adhesive bonding or thermal bonding as described in further detail below. As shown in FIG. 4, sub-webs 10a, 10b, 10c are separated in a second direction D2 perpendicular to the first direction D1 and joined to the carrier 40 without offsetting the sub-webs in the first direction D1. In other words, the sawtooth pattern is synchronized in sub-webs 10a, 10b, 10c.

The carrier 40 may be continuous (i.e., without any through-penetrating holes) or discontinuous (e.g. comprising through-penetrating perforations or pores). The carrier may comprise a variety of suitable materials including woven webs, non-woven webs (e.g., spunbond webs, spun-laced webs, airlaid webs, meltblown web, and bonded carded webs), textiles, plastic films (e.g., single- or multi-layered films, coextruded films, laterally laminated films, or films comprising foam layers), and combinations thereof. In some embodiments, the carrier is a fibrous material (e.g., a woven, nonwoven, or knit material). In some embodiments, the carrier comprises multiple layers of nonwoven materials with, for example, at least one layer of a meltblown nonwoven and at least one layer of a spunbonded nonwoven, or any other suitable combination of nonwoven materials. For example, the carrier may be a spunbond-meltblown-spunbond, spunbond-spunbond, or spunbond-spunbond-spunbond multilayer material. Or, the carrier may be a composite web comprising a nonwoven layer and a dense film layer. Fibrous materials that may provide useful carriers may be made from any of the fibers described above as useful for making loop materials. Useful carriers may have any suitable basis weight or thickness that is desired for a particular application. For a fibrous carrier, the basis weight may range, e.g., from at least about 5, 8, 10, 20, 30, or 40 grams per square meter, up to about 400, 200, or 100 grams per square meter. The carrier may be up to about 5 mm, about 2 mm, or about 1 mm in thickness and/or at least about 0.1, about 0.2, or about 0.5 mm in thickness.

In some embodiments, one or more zones of the carrier may comprise one or more elastically extensible materials extending in at least one direction when a force is applied and returning to approximately their original dimension after the force is removed. However, in some embodiments, at least the portion of the carrier joined to the sub-webs is not stretchable. In some embodiments, the portion of carrier joined to the sub-webs will have up to a 10 (in some embodiments, up to 9, 8, 7, 6, or 5) percent elongation in the second direction D2. In some embodiments, the carrier may be extensible but nonelastic. In other words, the carrier may have an elongation of at least 5, 10, 15, 20, 25, 30, 40, or 50 percent but substantially no recovery from the elongation (e.g., up to 10 or 5 percent recovery). Suitable extensible carriers may include nonwovens (e.g., spunbond, spunbond meltblown spunbond, or carded nonwovens). In some embodiments, the nonwoven may be a high elongation carded nonwoven (e.g., HEC).

Figure 5:
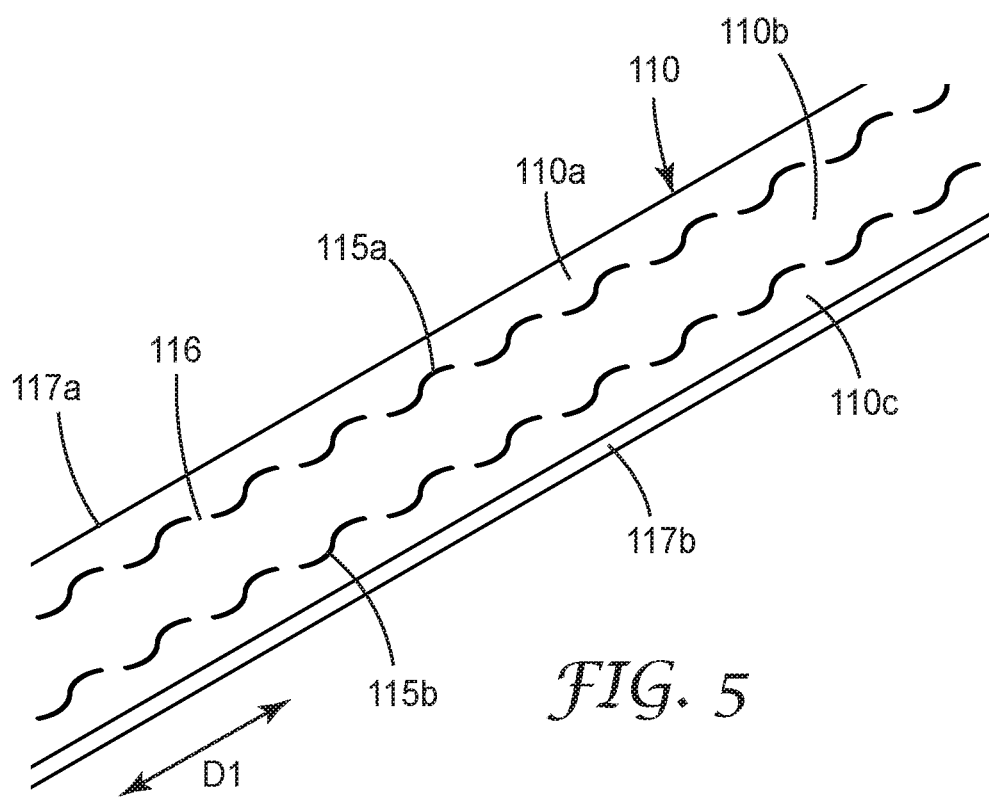
FIG. 5 is a perspective view of an embodiment of a portion of a web useful for the method of making a laminate disclosed herein, in which the web has two nonlinear lines of weakness.

FIG. 5 illustrates an example of a portion of a thermoplastic web 110 with nonlinear lines of weakness 115a, 115b that is useful for practicing the method disclosed herein. In the illustrated embodiment, the mechanical fastening elements of the thermoplastic web 110 are not shown. In some embodiments, including the embodiment illustrated in FIG. 5, the nonlinear lines of weakness 115a, 115b have a wave shape that is curved (e.g., a sine wave). The nonlinear lines of weakness 115a, 115b extend predominantly in the direction D1 of the running web (the machine direction MD). The nonlinear lines of weakness 115a, 115b are in the form of a series of perforations, and the thermoplastic web 110 includes connection points 116 where the thermoplastic web 110 is not cut through. Thermoplastic web 110 also has two opposing straight longitudinal outer edges 117a, 117b. In the embodiment illustrated in FIG. 5, there are at least two nonlinear lines of weakness 115a, 115b demarcating nonlinear edges of at least three sub-webs 110a, 110b, 110c of the thermoplastic web without severing the web.

Figure 6:
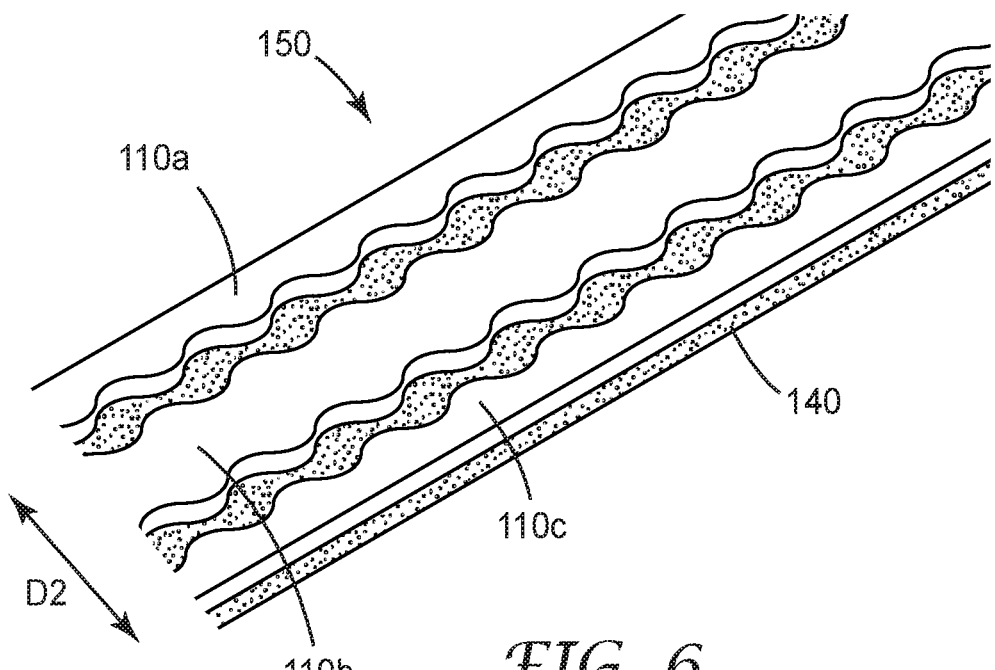
FIG. 6 is a perspective view of an embodiment of a laminate made from the web of FIG. 5 using an embodiment of the method of the present disclosure.

FIG. 6 illustrates a laminate 150 made from the thermoplastic web shown in FIG. 5 using an embodiment of the method of the present disclosure. After severing the thermoplastic web 110 at the nonlinear lines of weakness 115a, 115b, the sub-webs 110a, 110b, 110c are joined to a carrier 140 using any of the methods described below. As shown in FIG. 6, sub-webs 110a, 110b, 110c are separated in a second direction D2 perpendicular to the first propagation direction D1 and joined to the carrier 140 without offsetting the sub-webs in the first propagation direction D1. In other words, the sine wave pattern is synchronized in sub-webs 110a, 110b, 110c.

Figure 7:
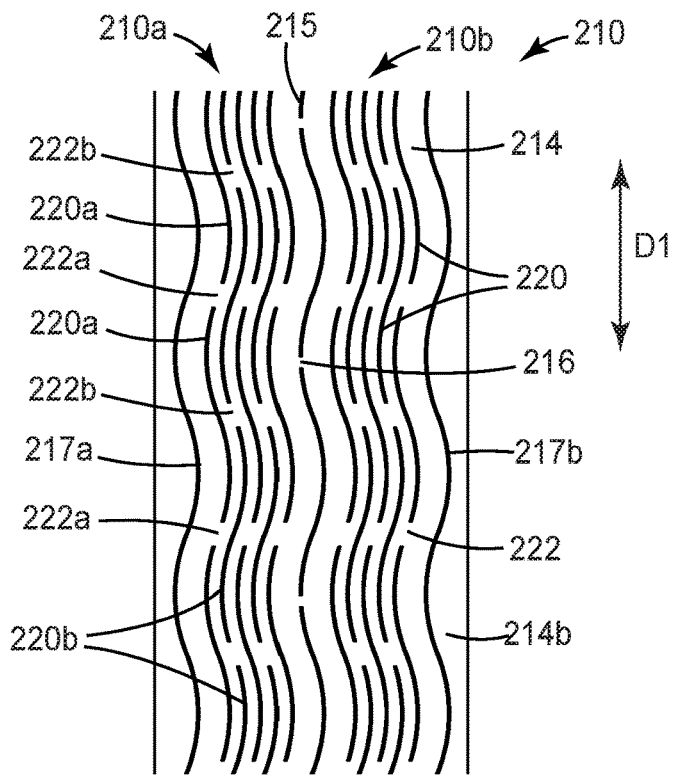
FIG. 7 is a top view of an embodiment of a portion of a web useful for the method of making a laminate disclosed herein, in which the web has a nonlinear line of weakness forming two sub-webs, each having a plurality of laterally spaced interrupted slits.

In some embodiments, each of the at least two sub-webs includes further slits, distinct from the nonlinear lines of weakness. FIG. 7 illustrates another embodiment of a thermoplastic web 210 useful for the method of making a laminate of the present disclosure. In the embodiment illustrated in FIG. 7, each of the two sub-webs 210a, 210b demarcated by nonlinear line of weakness 215 includes a plurality of laterally separated interrupted slits 220 cut through the backing 214 that are interrupted by intact bridging regions 222 of the sub-web. The bridging regions 222 are regions where the sub-web is not cut through. The intact bridging regions 222 divide the interrupted slits 220 into a series of spaced apart slit portions 220a. The interrupted slits are nonlinear and, in the illustrated embodiment, extend in the same direction as the nonlinear line of weakness 215. The shape of the interrupted slits 220 may be the same or different from the nonlinear lines of weakness 215 and can be any of the shapes described above for the nonlinear lines of weakness. In the illustrated embodiment, the nonlinear line of weakness 215 and the interrupted slits 220 are in the shape of a sine wave. Thermoplastic web 210 also has nonlinear opposing side edges 217a, 217b, which may have the same or different shape than the nonlinear line of weakness and/or interrupted slits. In the embodiment illustrated in FIG. 7, each of the nonlinear side edges 217a, 217b, the nonlinear line of weakness 215, and the interrupted slits 220 has the same shape. Side edges 217a, 217b can be formed from continuous cuts in thermoplastic web 210 followed by removal of the backing trim 214b. In the illustrated embodiment, the mechanical fastening elements of the thermoplastic web 210 are not shown.

The spaced apart slit portions 220a and 220b and consequently bridging regions 222a and 222b of adjacent interrupted slits are offset in the first direction. The bridging regions are offset such that bridging region 222b is located substantially midway between bridging regions 222a in the first direction D1. However, in some embodiments, the interrupted slits 220 and bridging regions 222, 222a, and 222b may be positioned in other arrangements.

Figure 8:
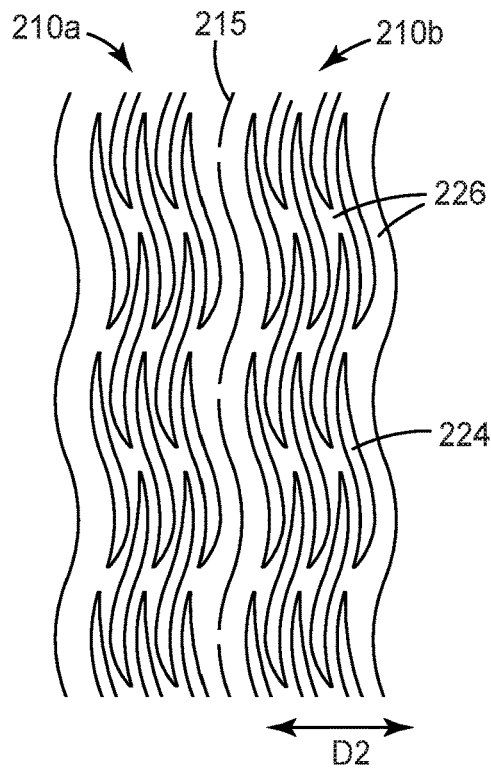
FIG. 8 is a top view of the web shown in FIG. 7 after spreading the two sub-webs but before severing the thermoplastic web at the nonlinear line of weakness.

FIG. 8 illustrates the effect of spreading the slit thermoplastic web like that shown in FIG. 7 before severing the thermoplastic web at the nonlinear line of weakness. When the slit sub-webs 210a, 210b are spread in the direction D2, multiple strands 226 of the backing are provided, and the separation between at least some of the multiple strands creates openings 224. The method according to the present disclosure typically increases the width of the slit thermoplastic web (that is, the dimension in the direction D2). In some embodiments, the width of the at least two connected spread mechanical fastening strips is at least 5, 10, 15, 20, or 25 percent greater than the width of the input slit web. In some embodiments, the width of the at least two connected spread mechanical fastening strips is up to 40, 50, 75, 100, 150, or 200 percent greater than the width of the input slit web.

The particular arrangement of the bridging regions 222, 222a, and 222b can be designed, for example, based on the desired length of the slit portions 220a and the amount of spreading desired for the multiple strands 226. Various lengths of bridging regions 222, 222a, and 222b may be useful. In some embodiments, any bridging regions 222 in a given interrupted slit 220 have a combined length in the direction of the interrupted slit of up to 50 (in some embodiments, 40, 30, 25, 20, 15, or 10) percent of the length of the slit web in the first direction (D1). In some embodiments, for maximizing the ability of the sub-web 210a to spread, it may be desirable to minimize the combined length of the bridging regions in the direction of the interrupted slit. Minimizing the combined length of the bridging regions 222 in the direction of the interrupted slit may be accomplished by at least one of minimizing the length of any particular bridging region 222 or maximizing the distance between bridging regions 222. In some embodiments, the length of one bridging region, measured as the shortest distance between slit portions 220a, is up to 3, 2, or 1.5 mm and at least 0.25, 0.5, or 0.75 mm. In some embodiments, the number of bridging regions along the length of the sub-web 210a, 210b in the direction of the interrupted slit is up to 1.5, 1.25, 1.0, 0.75, 0.60, or 0.5 per cm. The distance between bridging regions 222 in the direction of the interrupted slit may be, for example, at least 0.75, 1.0, 1.25, 1.5, or 1.75 cm. Furthermore, the length of the interrupted slit portions between bridging regions can be adjusted and may be selected to maximize the distance between bridging regions. In some embodiments, the length of the slit portions 220a, 220b is at least 8 (in some embodiments, at least 10, 12, 14, 15, 16, 17, 18, 19, or 20) mm, as measured as the straight-line distance between the ends of the slit portions 220a, 220b.

In the embodiment illustrated in FIG. 7, the interrupted slits 220 of the sub-webs 210a, 210b useful for practicing the present disclosure have shorter slit portions 220a, 220b than the nonlinear line of weakness 215. The connection points 216 are shorter than the bridging regions 222. The short connection points 216 are designed to allow easy separation of the two sub-webs 210a, 210b. On the other hand, the longer bridging regions 222 can hold together the strands 226 of the sub-webs formed by spreading the sub-webs in the direction D2, shown in FIG. 8.

In some embodiments, slit portions 220a, 220b have a regular pattern that repeats down the sub-web 210a, 210b. In some embodiments, spacing (e.g., in the first direction D1) between slit portions 220a may be uniform or substantially uniform (that is, the spacing may differ by up to 2 percent, 1 percent, or less than 1 or 0.5 percent) although this is not a requirement. In some embodiments, slit portions 220a have different lengths than slit portions 220b of adjacent slits, which results in openings 224 having different sizes after the sub-webs are spread. That is, shorter slit portions 220a result in shorter openings 224 in the first direction D1. The slit portions of the smaller size and slit portions of the larger size each may be aligned with each other across the sub-webs, or, in other embodiments, slits of the same size may be offset relative to each other in a regular pattern. Furthermore, the length of the bridging regions 222 may be made to vary within a strand 226 or between strands 226 as desired for a particular application or appearance. In some embodiments, slit portions have different lengths in different zones in the CD of the slit web. The multiple strands 226 can have a different appearance from each other in the same spread mechanical fastening strip.

For any of the embodiments of the method of making a laminate disclosed herein, the number of interrupted slits and resulting openings may be adjusted depending on the desired spread mechanical fastening strips. The interrupted slits may be evenly spaced or unevenly spaced as desired. In some embodiments, there are up to 10, 9, 8, 7, 6, 5, 4, 3, 2, or 1 interrupted slits per 10 mm across the width of the sub-webs 210a, 210b in the second direction (D2). Typically, the width dimension of each of the multiple strands 226 formed between interrupted slits is wider than at least the bases of the upstanding posts of male fastening elements (not shown). In the illustrated embodiment, the interrupted slits 220 are evenly spaced and centered in the sub-webs 210a, 210b. For interrupted slits that are evenly spaced, the spacing (e.g., distance in D2) between the interrupted slits may differ by up to 10, 5, 2.5, or 1 percent.

For any of the embodiments of the method of making a laminate disclosed herein in which the sub-webs include interrupted slits, the openings formed by the separation of the multiple strands between at least some of the bridging regions are in the form of a repeating pattern of geometric shapes. In the embodiments illustrated in FIGS. 7 and 8, the geometric shapes have elongated S shapes. In some embodiments (e.g., some embodiments in which the shape of the interrupted slits are at least partially rectilinear), the geometric shapes are polygons. In some embodiments of the spread mechanical fastening web, including the embodiment illustrated in FIG. 8, the multiple strands 226 of the web attached to each other at least at some of the intact bridging regions form an angle β of less than 90 degrees, in some embodiments, up to 60 degrees, 45 degrees, or 20 degrees, and in some embodiments, in a range from 0.5 to 20 degrees or in a range from about 0.5 to 10 degrees. As described above, there may be more than one repeating pattern of geometric shaped openings. The openings may be evenly spaced or unevenly spaced as desired. For openings that are evenly spaced, the spacing (e.g., distance in D2) between the openings may differ by up to 10, 5, 2.5, or 1 percent.

Figure 9:
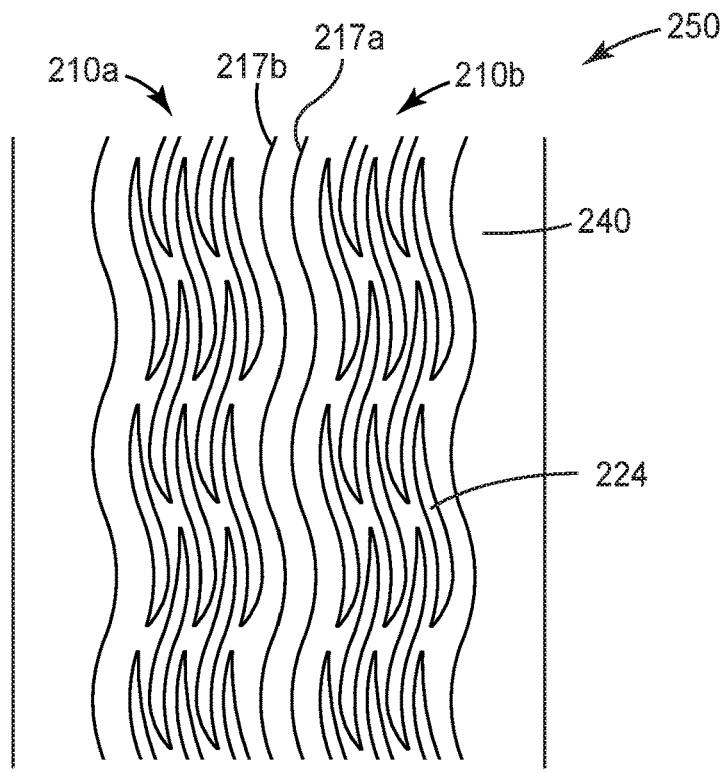
FIG. 9 is a top view of an embodiment of a laminate made from the web of FIG. 7 using an embodiment of the method of the present disclosure.

FIG. 9 illustrates a laminate 250 made from the thermoplastic web shown in FIG. 8 using an embodiment of the method of the present disclosure. After severing the thermoplastic web at the nonlinear lines of weakness 215, the sub-webs 210a, 210b are joined to a carrier 240 using any of the methods described below. As shown in FIG. 9, sub-webs 210a, 210b are separated in a second direction D2 perpendicular to the first direction D1 such that side edge 217b of sub-web 210a is separated from side edge 217a of sub-web 210b on the carrier 240. The sub-webs 210a, 210b are joined to the carrier 240 without offsetting the sub-webs in the first propagation direction D1. In other words, the sine wave pattern is synchronized in sub-webs 210a, 210b.

Although the methods of making a laminate as illustrated in FIGS. 4, 6, and 9 each show nonlinear lines of weakness extending predominantly in the MD of the thermoplastic web, nonlinear lines of weakness may be made in any desired direction. For example, nonlinear lines of weakness may be made at an angle from 1 to 85 degrees to the MD of the thermoplastic web. In some embodiments, nonlinear lines of weakness are made at an angle in a range from 35 to 55 degrees (e.g., 45 degrees) to the MD of the thermoplastic web.

The method according to the present disclosure may be useful for any width of the thermoplastic web in the CD. In some embodiments, the thermoplastic web has a width in the CD in a range from 1 cm to 50 cm, 1 cm to 25 cm, or 1 cm to 10 cm wide.

The fastening laminates made by the methods disclosed herein are useful, for example, in absorbent articles. Absorbent articles may have at least a front waist region, a rear waist region, and a longitudinal center line bisecting the front waist region and the rear waist region, wherein at least one of the front waist region or the rear waist region comprises the fastening laminate disclosed herein. The fastening laminate may be in the form of a fastening tab or landing zone that is bonded to at least one of the front waist region or the rear waist region. A fastening tab may extend outwardly from at least one of the left longitudinal edge or the right longitudinal edge of the absorbent article. In other embodiments, the fastening laminate may be an integral ear portion of the absorbent article. The carrier at the user's end of a fastening tab may exceed the extension of the spread mechanical fastening strips thereby providing a fingerlift. The fastening laminate made by the methods disclosed herein may also be useful, for example, for disposable articles such as sanitary napkins.

In some embodiments, the method according to the present disclosure includes cutting the laminate in the CD or other direction non-parallel to the first direction to provide a fastening tab.

Figure 10:
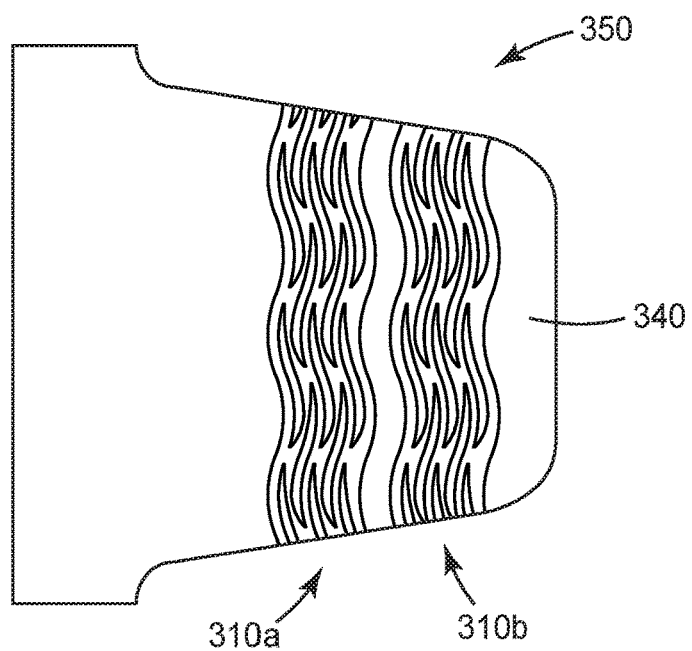
FIG. 10 is a top view of an embodiment of a fastening laminate made from an embodiment of the method of the present disclosure.

A laminate useful as a fastening tab for an absorbent article is shown in FIG. 10. FIG. 10 illustrates a laminate 350 made from the thermoplastic web similar to that shown in FIG. 7 using an embodiment of the method of the present disclosure. After severing the thermoplastic web at the nonlinear line of weakness, the sub-webs 310a, 310b are joined to a carrier 340 using any of the methods described below. As shown in FIG. 10, sub-webs 310a, 310b are separated and joined to the carrier 240 without offsetting the sub-webs in the first propagation direction. In other words, the sine wave pattern is synchronized in sub-webs 310a, 310b.

The mechanical fastening laminates made by the method of the present disclosure may also be useful in many other fastening applications, for example, assembly of automotive parts or any other application in which releasable attachment may be desirable.

Figure 11:
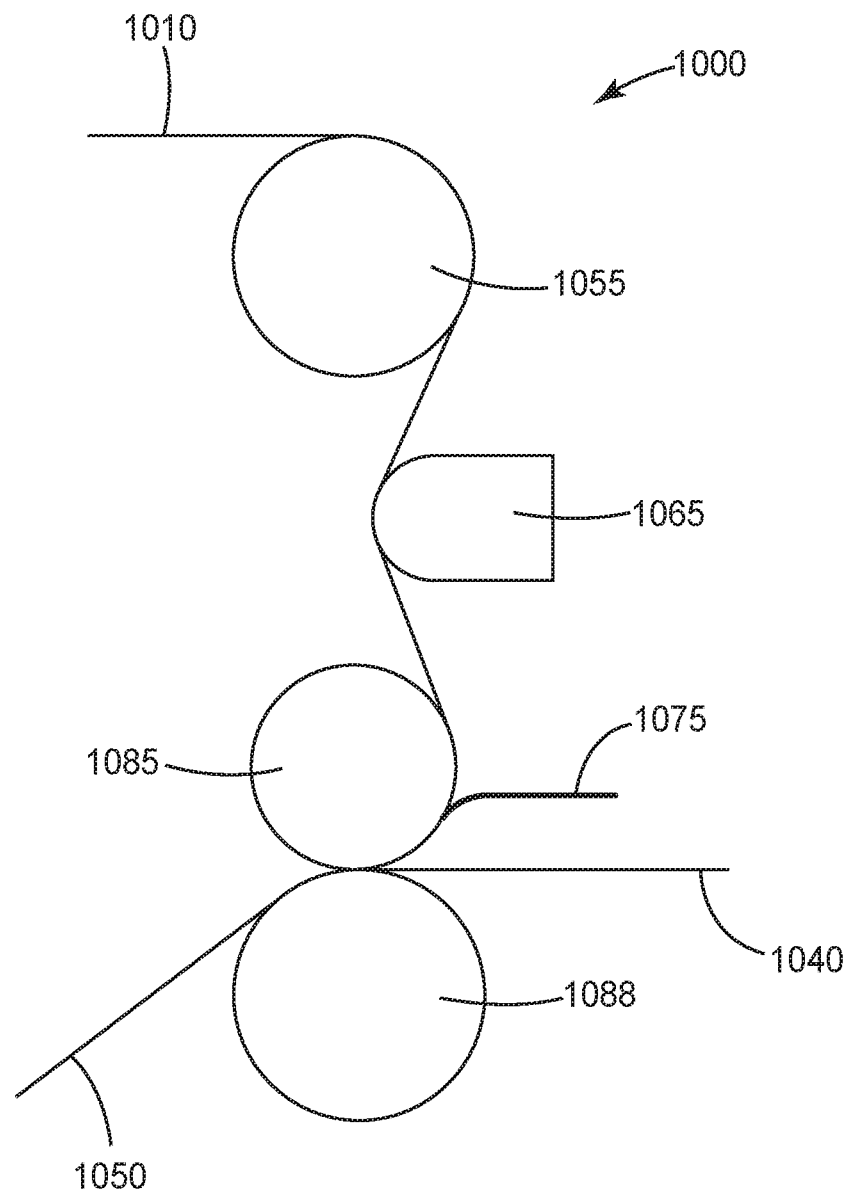
FIG. 11 is a diagrammatical view of an embodiment of carrying out the method of making a laminate disclosed herein.

A diagrammatical representation of an embodiment of an apparatus 1000 for carrying out the method of the present disclosure is shown in FIG. 11. In FIG. 11, thermoplastic web 1010 is directed over roller 1055, which may be useful, for example, for adjusting the tension in the web 1010. In the illustrated embodiment, the thermoplastic web includes at least one nonlinear line of weakness (not shown) that demarcates nonlinear edges of at least two sub-webs. Each of the sub-webs includes a plurality of laterally separated interrupted slits that are interrupted by intact bridging regions of the sub-web. In the illustrated embodiment, the thermoplastic web 1010 is then spread by moving it over crowned surface 1065 to provide at least two connected spread mechanical fastening strips.

In this application, a crowned surface can be considered any forming surface that lengthens the path of a portion of the thermoplastic web 1010. A crowned surface useful for practicing the present disclosure has a varying height dimension in a direction corresponding to the second direction D2 of the thermoplastic web. Generally, the height of the crowned surface is greatest at its center. The crowned surface may be a smooth surface having a generally spherical or elliptical shape in which the diameter or axis continuously increases toward its center. However, a crowned surface useful for practicing the present disclosure need not have a uniform height variation over its entire portion that contacts the thermoplastic web. For example, the crown surface may have a flat portion where the slit web first contacts it, and the curvature of the crowned surface in a direction corresponding to the CD of the thermoplastic web may increase in the direction of the thermoplastic web path. A flat portion can serve as an entry point for the slit sub-webs, and as the curvature of the crowned surface increases in the width direction, the component of the normal force in the second direction imparted by the crowned surface onto the slit sub-webs increases as the slit sub-webs move along the path from a flat surface to a region with more curvature. The crowned surface may also have, in some embodiments, ridges or other surface irregularities.

Any surface over which a web in tension is bent or wrapped around is believed to impart a force on the web that is normal or perpendicular to the web. Because of the varying height of a crowned surface, the force imparted on a web by a crowned surface is not evenly distributed. Without wanting to be bound by theory, it is believed that the crowned surface can spread open the sub-webs having interrupted slits as described herein because a component of the normal force generated by a crowned surface will be in the cross-web direction. The cross-direction strength of the sub-webs is relatively low because of the slits in the web, and the amount of tension in the web that would resist spreading is low. Therefore, the cross-directional component of the force generated by a crowned surface can induce spreading of slit sub-webs.

The amount of spreading that can result by moving the slit sub-webs over a crowned surface can be limited by the frictional force resisting the cross-directional movement of the spreading web. Because of this, it may be desirable to minimize the friction between the thermoplastic web and the crowned surface. Such friction can be decreased if at least a portion of the crowned surface is a low-friction surface. For example, a least a portion of the crowned surface can be made from a low-friction material or can be coated with a low-friction coating. In some embodiments, crowned surface 1065 can be made from a low-friction material such as smooth or polished metal (e.g., aluminum or steel), smooth plastic (e.g., polytetrafluoroethylene, polyoxymethylene, polyether ether ketone, or other engineering plastics), or a smooth plastic composite material. In some embodiments, crowned surface 1065 can be coated with a low-friction coating (e.g., plasma or polytetrafluoroethylene coating).

Also, if the crowned surface is an air bearing, friction between the slit sub-webs and the crowned surface may be decreased. Since the coefficient of kinetic friction of two materials is generally lower than the corresponding coefficient of static friction, it is typically desirable that the crowned surface and the slit web are not moving at the same speed in the same direction so that the crowned surface and the slit web can have a "slipping" interface. Accordingly, in some embodiments, the crowned surface does not rotate, or, in other words, it is stationary. In other embodiments, the crowned surface may be rotating in a direction opposite to the direction of the slit sub-webs or can be rotating at a different speed than the slit sub-webs in the machine direction.

Various web handling and design techniques may be useful for decreasing the tendency of the slit web to slide off of the crowned surface, for example, if the cross-directional force in one direction becomes greater for some reason than the cross-directional force in the opposite direction. Guiding mechanisms and minimizing the size of the crowned surface to get the desired amount of spreading of the slit web may be desirable. Also positioning upstream and downstream rollers 1055 and 1085 close to the crowned surface 1065 may be useful as well as positioning the rollers such that the slit web bends over or wraps around a minimal portion of the crowned surface. Each of these may be useful alone or in combination.

The amount of spreading provided in some embodiments of the method disclosed herein can be controlled by a variety of factors including the geometry of the crowned surface, the amount of tension in the machine direction, and the coefficient of friction between the two sub-webs and the crowned surface as described above. If only a single crowned surface is used in the method disclosed herein, the width of the two, connected spread mechanical fastening strips is typically up to 40, 50, 75, or 100 percent greater than the width of the input slit-sub-web.

For additional information about crown surfaces useful for practicing at least some embodiments of the method of the present disclosure, see, for example, U.S. Pat. No. 9,687,048 (Gilbert).

Referring again to FIG. 11, the method of the present disclosure includes severing the thermoplastic web at the nonlinear line(s) of weakness using a severing implement 1075. In some embodiments, including the illustrated embodiment, the severing implement 1075 can be at least one of a wire, shim, fin, blade, or a machine finger. A wide variety of solid objects having a thin shape may be useful for severing the thermoplastic web. Severing the web is typically carried out, for example, by contacting at least a portion of the nonlinear line of weakness with the severing implement. The severing implement can be made from any suitable material (e.g., metal or polymer). In the case of a wire, the wire can be stiff like a needle or more flexible like a guitar string. In some embodiments, the crowned surface can include at least one ridge as a severing implement for simultaneous spreading the sub-webs and severing the thermoplastic web at the nonlinear line(s) of weakness.

In the illustrated embodiment, the spread mechanical fastening strips are then laminated to a carrier web 1040 to form a laminate 1050. Lamination is carried out in a nip formed by rollers 1085 and 1088.

The spread mechanical fastening strips may be joined to a carrier, for example, by lamination (e.g., extrusion lamination), adhesives (e.g., pressure sensitive adhesives), or thermal bonding methods (e.g., ultrasonic bonding, calendering, bonding with a heated fluid, or surface bonding).

In some embodiments wherein the spread mechanical fastening strips are joined to a carrier, the carrier is provided with a layer of adhesive. In some of these embodiments, the spread mechanical fastening strips are bonded to the carrier with the adhesive to form a laminate, and the adhesive is exposed between the multiple strands in the laminate. When the laminate is used in a fastening tab, exposed adhesive that may be present in some embodiments between the multiple strands of the spread mechanical fastening strips may be useful for "anti-flagging" or for maintaining the disposable absorbent article in a rolled up state after use. Also when the laminate is used as a landing zone or fastening tab, exposed adhesive that may be present in some embodiments between the multiple strands of the spread mechanical fastening strips may be useful to provide a combination of mechanical and adhesive fastening.

In some embodiments, the thermoplastic backing can be joined to a fibrous web carrier using surface bonding or loft-retaining bonding techniques. The term "surface-bonded" when referring to the bonding of fibrous materials means that parts of fiber surfaces of at least portions of fibers are melt-bonded to the second surface of the backing, in such a manner as to substantially preserve the original (pre-bonded) shape of the second surface of the backing, and to substantially preserve at least some portions of the second surface of the backing in an exposed condition, in the surface-bonded area. Quantitatively, surface-bonded fibers may be distinguished from embedded fibers in that at least about 65% of the surface area of the surface-bonded fiber is visible above the second surface of the backing in the bonded portion of the fiber. Inspection from more than one angle may be necessary to visualize the entirety of the surface area of the fiber. The term "loft-retaining bond" when referring to the bonding of fibrous materials means a bonded fibrous material comprises a loft that is at least 80% of the loft exhibited by the material prior to, or in the absence of, the bonding process. The loft of a fibrous material as used herein is the ratio of the total volume occupied by the web (including fibers as well as interstitial spaces of the material that are not occupied by fibers) to the volume occupied by the material of the fibers alone. If only a portion of a fibrous web has the second surface of the backing bonded thereto, the retained loft can be easily ascertained by comparing the loft of the fibrous web in the bonded area to that of the web in an unbonded area. It may be convenient in some circumstances to compare the loft of the bonded web to that of a sample of the same web before being bonded, for example, if the entirety of fibrous web has the second surface of the backing bonded thereto.

In some embodiments, the joining the two sub-webs to a carrier to form the laminate comprises impinging heated fluid (e.g., ambient air, dehumidified air, nitrogen, an inert gas, or other gas mixture) onto at least one of the sub-webs or the carrier. In some embodiments, the heated fluid is heated air. In some embodiments, joining the two sub-webs to the carrier comprises impinging heated fluid onto a first surface of the fibrous web carrier while it is moving and/or impinging heated fluid onto the second surface of the sub-webs while the continuous web is moving, wherein the second surface is opposite the fibrous layer, loop, or upstanding posts the backing; and contacting the first surface of the fibrous web with the second surface of the sub-webs so that the first surface of the fibrous web is melt-bonded (e.g., surface-bonded or bonded with a loft-retaining bond) to the second surface of the sub-webs. Impinging heated fluid onto the first surface of the fibrous web and impinging gaseous fluid on the second surface of the sub-webs may be carried out sequentially or simultaneously. In some embodiments, the joining method includes impinging gaseous fluid on the second surface of the sub-webs, and moving the carrier through ambient-temperature quiescent air before contacting the first surface of the carrier with the second surface of the sub-webs so that the first surface of the carrier is melt-bonded to the second surface of the sub-webs. Further methods and apparatus for joining a continuous web to a fibrous carrier web using high-temperature impingement fluid are described in U.S. Pat. No. 9,096,960 (Biegler et al.), U.S. Pat. No. 9,126,224 (Biegler et al.), and U.S. Pat. No. 8,956,496 (Biegler et al.).

Although a crown surface described above is useful for spreading the slit sub-webs to in the second direction to provide two connected spread mechanical fastening strips, spreading the slit sub-webs can also be carried out by moving the slit sub-webs over diverging disks, a stretching surface, or one or more bowed rollers.

Useful diverging disks for spreading the slit sub-webs are spaced apart laterally and can have a support surface between them although the support surface is not required. The support surface may be connected to the two diverging disks with the diverging disks and support surface together forming an integral roller. Shafts may be useful, in some embodiments, for mounting and/or rotating the diverging disks although other mechanisms for mounting and rotating the disks are possible. The support surface may be useful, for example, for exerting a force normal to the web on the slit web. The support surface may be flush with the peripheral surfaces of the diverging disks around the entire periphery of the diverging disks or may bulge outward around the entire periphery of the diverging disks. However, in other embodiments, the support surface may be present only on one side of diverging disks. In other words, the support surface may extend to the peripheral surface for only a portion of the diverging disks.

The diverging disks and the support surface may be made from the same or different materials. In some embodiments, they both can be made of metal (e.g., aluminum or steel). In some embodiments, the diverging disks can be made from a high-friction material (e.g., a rubbery material), and the support surface can be made from a low-friction material (e.g., such as those described above) or provided with a low-friction coating.

Various methods may be useful for holding the side edges of the slit sub-webs 1010 to the peripheral surfaces of the diverging disks. For example, the side edges of the slit sub-webs can be held to the peripheral surfaces of the diverging disks using belts, pins, vacuum, forced air jets, or any combination of these methods.

In some embodiments, spreading the slit sub-webs is carried out by moving the two sub-webs over a stretching surface. With traction between the slit sub-webs and the stretching surface, the slit sub-webs spread apart as the stretching surface stretches. The stretching surface can be attached, for example, to two rotating diverging disks that are laterally spaced. The two rotating diverging disks may be included in a roller, for example. The stretchable surface can be provided, for example, by stretchable bands that are wrapped around corresponding pins on the two diverging disks. For example, a stretchable band can be wrapped around a pair of pins on opposing diverging disks where the two pins on the two disks are aligned with each other along the circumference of the disks. Multiple bands around the circumference of the diverging disks may be useful to allow the continuous movement of the slit web. Other stretchable surfaces are useful in conjunction with rotating diverging disks. For example, non-circular bands, tubing, or a coiled spring may provide the stretchable surface. Hollow tubing can have an inner diameter that allows it to be press fit on pins on the two diverging disks. The coiled spring may be metal (e.g., aluminum or steel) although other materials may be useful. The coiled spring may be coated with a high-friction coating, if desired. The high-friction coating can be, for example, a coating of an elastomeric material or a plasma coating known to provide a high-friction surface. Suitable plasma coatings include those available, for example, from Plasma Coating, Middlebury, Conn., under product family designations "10000" and "10015". In another example, a stretchable sleeve attached to the two diverging disks may be useful. Such a stretchable sleeve may be supported by a surface between the two diverging disks if desired, but this is not a requirement. An example of a tubular sleeve and clamps that may be adapted for use in the method according to the present disclosure is described in U.S. Pat. No. 4,862,565 (Damour). In this reference, a spreader roll with a resilient sleeve has been reported to be useful for removing wrinkles from fast traveling webs of fabric or plastic. Bands, tubing, coiled springs, or a sleeve may be attached to the diverging disks by pins clamps, belts, or any other of a variety of useful methods.

Any stretchable material that is capable of stretching and retracting during the rotation of the diverging disks may be useful for the stretchable surface. Such materials are elastic according to the definition provided above. In some embodiments, the stretchable surface is made from an elastomer. Examples of suitable classes of elastomers include natural polyisoprene, synthetic polyisoprene, polybutadiene, poly (2,3-dimethylbutadiene), poly(butadiene-co-pentadiene), polysulfide elastomers, butyl rubber (e.g., polyisobutylene copolymers with isoprene), halogenated butyl rubber, polychloroprene, poly(butadiene-co-nitrile), hydrogenated nitrile-butadiene copolymers, polyurethane, polyester urethane, and combinations thereof, any of which may be crosslinked by sulfur or non-sulfur vulcanization. Further useful elastomers include ethylene-propylene copolymers, ethylene-propylene-diene terpolymers, sulfonated ethylene-propylene-diene terpolymers, chlorosulfonated polyethylenes, silicone elastomers, acrylic elastomers, ethylene-acrylate copolymers, fluorinated elastomers, fluorochlorinated elastomers, fluorobrominated elastomers, and combinations thereof. Suitable elastomers also include thermoplastic elastomers, which are typically made up of blocks of glassy or crystalline blocks (e.g., polystyrene, poly(vinyltoluene), poly(t-butylstyrene), and polyester) and elastomeric blocks (e.g., polybutadiene, polyisoprene, ethylene-propylene copolymers, ethylene-butylene copolymers, polyether ester, and combinations thereof). Some thermoplastic elastomers are commercially available, for example, poly(styrene-butadiene-styrene) block copolymers marketed by Kraton Performance Polymers, Houston, Tex., under the trade designation "KRATON". The diverging disks themselves are typically made of metal (e.g., aluminum or steel) although other materials may be useful. Any of the embodiments of stretchable surfaces described above (e.g., bands, tubing, and sleeves) may be made of any of these materials. Combinations of different elastomers and different stretchable surfaces (e.g., bands, tubing, and sleeves) on the same or different pairs of diverging disks may be useful.

Typically, elastomeric materials such as any of those described above are considered "high-friction" materials and may allow for sufficient traction between the slit sub-webs and the stretching surface so that the slit sub-webs spread apart along with the stretching surface. The particular elastomer in the stretching surface may be selected to maximize the traction with the slit sub-webs. However, in some embodiments, it may be useful to increase the traction between a given elastomer and the slit sub-webs. This may be carried out, for example, by increasing the machine direction tension on the web, providing surface structure on the stretching surface, or directing male fastening elements in some embodiments of the slit sub-webs to face against the stretching surface to increase traction.

In operation, the stretching surface stretches for 180 degrees of the rotation of the diverging disks as it moves from the position where the disks are closest together to the position where the disks are furthest apart. The stretching surface then retracts for 180 degrees of the rotation of the diverging disks as it moves from the position where the disks are furthest apart to the position where the disks are closest together. Multiple strands of slit sub-webs that come into contact with the stretching surface at any position where the band is stretching will be spread apart in the direction of the stretch. The slit sub-webs may be positioned to be in contact with the stretching surface for any portion of the rotation sufficient to at least partially separate at least some of the multiple strands of the slit sub-webs. In some embodiments, the slit sub-webs may be in contact with the roller for the entire 180 degrees during which the stretchable surface is stretching. However, in some embodiments, it is sufficient for the slit sub-webs to remain in contact with the roller for any rotation in a range from 1 to 180 degrees, for example, up to 150, 120, 90, 60, 45, 30, 20, or 10 degrees of rotation, depending on the angle of the diverging disks and the amount of spreading desired in the slit sub-webs. In other embodiments, the slit sub-webs may remain in contact with the roller for any rotation in a range from 1 to 360 degrees depending on the amount of spreading desired. The wrap angle can be adjusted depending on the amount of spreading desired in the process.

While in some applications, it may be useful for the stretchable surface to be supported by a structure, for example, between the diverging disks that prevents or minimizes the inward deflection of the stretchable surface, such a support structure (e.g., a plurality of brushes) is not a requirement for the method disclosed herein. Without a support surface, the stretchable surface is permitted to deflect inward as the slit sub-webs contact the stretchable surface. A certain amount of deflection will not hamper the spreading effect of the stretchable surface.

For any of the embodiments described above in which diverging disks are used, the diverging disks may be positioned on a non-rotating shaft. The angle of the diverging disks can be set with adapters that are angled on the non-rotating shaft. Bearings can be useful for allowing rotation of the diverging disks on the non-rotating shaft. In other embodiments, the shaft itself may be angled so that the disks diverge. In some embodiments, the diverging disks are formed into a roller that is an idler roller, and the rotation of the diverging disks is not driven by any means other than the movement of the slit web. In other embodiments, the diverging disks may be driven by pulleys and belts or other suitable methods. In some embodiments, the rotation of the disks is driven from only one end of the shaft. In some embodiments, each of the shafts is driven at a desired speed to cause rotation of the disks. For any of the embodiments in which the rotation of the diverging disks is driven, a clutch mechanism may be useful for adjusting the speed of rotation.

Also for any of the embodiments described above in which diverging disks are used, diverging disks are positioned such that a portion of their peripheral surfaces have a closer spacing at one location and a larger spacing at a second location. The angle, which may be set by adapters, by the position of shafts, by an angle in a shaft, or by a combination thereof, can be selected depending on the desired amount of spread in the slit sub-webs. For example, each diverging disk may independently be angled at least 1, 2, 3, 4, or 5 degrees and up to 20, 15, or 10 degrees with respect to the machine direction of the running web. In some embodiments, each diverging disk is independently angled in a range from 1 to 10 degrees or 2.5 to 7.5 degrees. Since the diverging disks may be independently angled, the method according to the present disclosure may be useful for spreading the slit sub-webs uniformly or non-uniformly with respect to the center of the slit sub-webs. In some embodiments, the strands in one sub-web may be spread apart more than the strands in another sub-web.

The difference between the closest and largest spacing of the diverging disks affects the amount of spreading of the slit sub-webs. In some embodiments, the largest spacing d2 is at least 25, 50, 60, 70, 80, 90, or 100 percent greater than the closet spacing d1. The percentage that the d2 spacing is greater than the d1 spacing can be determined, for example, by the formula [(d2−d1)/d1]*100. The closer the spacing of the diverging disks, the more spreading of the slit sub-webs is allowed at a given angle of the diverging disks. Although other sizes may be useful, in some embodiments, d1 is at least 8 millimeters (mm) and up to 15.25 centimeters (cm), 12.7 cm, or 12.1 cm. Also, the larger the diverging disks, the more spreading of the slit sub-webs is possible at a given angle. In some embodiments, the disks have a diameter of at least 10, 12, 14, or 16 cm. The method according to the present disclosure is useful, in some embodiments, for spreading slit webs 1 cm to 50 cm wide, 1 cm to 25 cm wide, 1 cm to 10 cm wide, or up to 10 cm in width, and it is possible to achieve an increase in width of at least 5, 15, 20, or 25 percent and up to 40, 50, 75, 100, 150, or 200 percent.

For additional information about methods using diverging disks and stretching surfaces useful for practicing at least some embodiments of the method of the present disclosure, see, for example, U.S. Pat. No. 9,591,896 (Gilbert) and U.S. Pat. No. 9,314,962 (Rothwell).

In some embodiments, spreading the slit sub-webs is carried out by moving the two sub-webs over one or more bowed rollers. The bowed rollers may be covered with an elastomeric material as described above or may otherwise be provided with a high-friction surface. Examples of useful bowed roller include those described in U.S. Pat. No. 3,645,433 (Lucas); U.S. Pat. No. 5,791,030 (Aihara); and U.S. Pat. No. 6,843,762 (Munche).

Spread mechanical fastening strips can optionally be handled by one or more other rollers in addition to those shown schematically in FIG. 11. In some embodiments, before lamination, spread mechanical fastening web can be directed onto a rotating heated cylinder optionally followed by a rotating chilled cylinder to anneal and rapidly cool the spread mechanical fastening strips. In some embodiments, roller 1055 and any additional roller (not shown) may be a high-friction roller (e.g., comprising a rubbery material or a material with a rough surface). The high-friction roller may be heated or chilled, if desired, or may be useful at room temperature. A high-friction roller may be useful, for example, for holding the spread mechanical fastening strips in a spread configuration before lamination whether or not the web is annealed.

When the two sub-webs are joined to a carrier to form the laminate, the two sub-webs are separated in a second direction perpendicular to the first direction. The separation may be formed, for example, by necking in of the spread mechanical fastening strips after the nonlinear line of weakness is severed. Such necking can occur from the tension in the web. In some embodiments, the method of the present disclosure further comprises applying tension to the web in the first direction.

In some embodiments, the method according to the present disclosure further comprises heating the two-connected spread mechanical fastening strips. In some embodiments, the method according to the present disclosure further comprises annealing the two, connected spread mechanical fastening strips. In some embodiments, annealing comprises heating the two, connected spread mechanical fastening strips. In some embodiments, annealing comprises heating and then cooling (e.g., rapidly cooling) the spread mechanical fastening web to maintain its configuration. Heating and/or annealing can be carried out, for example, after the spread mechanical fastening strips have been spread to the final desired extent or at an intermediate stage, for example, if the spread mechanical fastening strips are spread a second time with a second crowned surface, pair of diverging disks, stretching surface, bowed roller, or combination thereof. Annealing can be useful, for example, depending on the extent of spreading, and can be useful to maintain the openings between multiple strands, for example, when the width of the slit sub-webs has been increased by at least 50 percent. Annealing can also be useful, for example, for maintaining at least some of the multiple strands in a substantially coplanar arrangement. In some embodiments, heating is only applied to the second surface of the spread mechanical fastening web (i.e., the surface opposite the first surface from which the mechanical fastening elements project) to minimize any damage to the mechanical fastening elements that may result from heating. Heating may be carried out on a continuous web, for example, using heated rollers, or using non-contact heating methods such as IR irradiation, hot air treatment, or by directing the web through a heated chamber.

Referring again to FIG. 11, which is useful for making a laminate in which each of the two sub-webs comprises a plurality of laterally separated interrupted slits that are interrupted by intact bridging regions of the sub-web such as that shown in FIGS. 9 and 10, at least one of the crown roller 1065 or the severing implement 1075 may be eliminated when the sub-webs do not include slits, for example, as shown in FIGS. 4 and 6. In other words, the thermoplastic web having at least one nonlinear line of weakness can be run directly from roller 1055 to the into the nip formed by rolls 1085 and 1088 after severing the web without including the step of spreading each of sub-webs. In some of these embodiments, severing the sub-webs is carried out with the severing implement 1075, which can be at least one of a wire, shim, fin, blade, or a machine finger. In other embodiments, the nonlinear line of weakness may be weak enough such that other methods may be useful to sever the thermoplastic web at the nonlinear line of weakness. For example, passing the thermoplastic web having a very weak nonlinear line of weakness over a crown surface 1065 such as described in any of the above embodiments may be useful for severing the thermoplastic web into the sub-webs. The other spreading methods described above in any of their embodiments (e.g., diverging disks, a stretching surface, or at least one bowed roller) may be useful for severing the thermoplastic web into the sub-webs.

When the two sub-webs are joined to a carrier to form the laminate, the two sub-webs are separated in a second direction perpendicular to the first direction. In embodiments in which the sub-webs do not include slits, the separation can be effected by increasing tension in the web. In some embodiments, the method of the present disclosure further comprises applying tension to the web in the first direction. In other embodiments, separation of the two sub-webs can be facilitated using a crown surface, diverging disks, stretching surface, or at least one bowed roller according to any of the embodiments described above. A high-friction roller may be useful, in some embodiments, for maintaining the separation between the sub-webs before lamination.

In some embodiments, the method of the present disclosure further includes forming the nonlinear line(s) of weakness in the thermoplastic web. Forming the nonlinear line(s) of weakness can be carried out in a variety of ways. For example, rotary die cutting of a continuous thermoplastic web having mechanical fastening elements may be useful. A series of perforations can be made, for example, by using rotary cutting blades having gaps to form the connection points 16. The height of the blade in the gaps may be adjusted to allow for the connection points to be partially cut or not cut at all, depending on the desired embodiment. Other cutting methods (e.g., laser cutting) may also be useful. Cutting can be performed from either surface of the continuous thermoplastic web. A series of perforations may be cut "through" the web having mechanical fastening elements, which means that the perforations cut through the entire thickness of the web.

In some embodiments, nonlinear lines of weakness in the form of partial-depth slits are formed simultaneously with the mechanical fastening elements (e.g., male fastening elements) during the molding or extrusion process described above for making mechanical fastening elements. For example, the partial-depth slits may be made using raised ridges on the forming roll used to make mechanical fastening elements or using a profiled die lip designed to form depressions in the thermoplastic web.

In some embodiments, the method of making a laminate according to the present disclosure includes slitting the thermoplastic web to provide the plurality of laterally separated interrupted slits. Any of the slitting methods described above for forming the nonlinear line(s) of weakness can be useful for forming the interrupted slits. For example, rotary die cutting and laser cutting may be useful. An interrupted slit can be made, for example, by using rotary cutting blades having gaps to form the bridging regions. The gaps in the rotary blades useful for making bridging regions may be longer than the gaps used to make the connection points in the nonlinear line(s) of weakness. The height of the blade in the gaps may be adjusted to allow for the connection points to be partially cut or not cut at all, depending on the desired embodiment.

When male fastening elements are formed as described above, for example, where a thermoplastic material is fed onto a continuously moving mold surface with cavities having the inverse shape of upstanding posts, forming the nonlinear line of weakness according to some embodiments of the method disclosed herein can be carried out before or after a capping step is carried out to form loop-engaging heads. Also, deforming the distal tip to form a cap can be carried out, for example, after slitting through the web but before spreading the slit web in embodiments in which the sub-webs include a plurality of interrupted slits. Deforming the distal tip to form a cap can be carried out, for example, after lamination, if desired. The formation of male fastening elements can also include a step in which the shape of the cap is changed, for example, as described in U.S. Pat. No. 6,132,660 (Kampfer). Such a cap modifying step can be carried out directly after capping or after any of forming the nonlinear line of weakness in the thermoplastic web, slitting, spreading, or laminating as described herein.

In some embodiments, the method of making a laminate according to the present disclosure includes providing the thermoplastic web by unwinding the thermoplastic web from a roll. The finished laminate may also be wound into a roll. Unwinding the thermoplastic web from a roll may also be carried out, in some embodiments, before the nonlinear line of weakness is formed in the web. In some of these embodiments, forming the nonlinear line of weakness in the thermoplastic web, severing the thermoplastic web and joining the two sub-webs to the carrier are all carried out in-line without offsetting the two sub-webs in the first propagation direction. In other embodiments, the nonlinear line of weakness may be provided in the thermoplastic web followed by winding into a roll until the method of the present disclosure is carried out.

Some Embodiments of the Disclosure

In a first embodiment, the present disclosure provides a method of making a laminate, the method comprising:

providing a thermoplastic web having mechanical fastening elements and a nonlinear line of weakness, wherein the nonlinear line of weakness extends predominantly in a first direction and demarcates nonlinear edges of two sub-webs but does not sever the thermoplastic web;

severing the thermoplastic web at the nonlinear line of weakness into the two sub-webs; and joining the two sub-webs to a carrier to form the laminate, wherein the two sub-webs are separated in a second direction perpendicular to the first direction, and wherein severing the thermoplastic web and joining the two sub-webs to the carrier are carried out in-line without offsetting the two sub-webs in the first direction.

In a second embodiment, the present disclosure provides the method of the first embodiment, wherein the nonlinear line of weakness has a wave shape.

In a third embodiment, the present disclosure the method of the first or second embodiment, wherein the thermoplastic web has two opposing nonlinear longitudinal outer edges.

In a fourth embodiment, the present disclosure provides the method of any one of the first to third embodiments, wherein the nonlinear line of weakness comprises a series of perforations.

In the fifth embodiment, the present disclosure provides the method of any one of the first to fourth embodiments, wherein the nonlinear line of weakness comprises a partial-depth cut.

In a sixth embodiment, the present disclosure provides the method of any one of the first to fifth embodiments, wherein each of the two sub-webs comprises a plurality of laterally separated interrupted slits that are interrupted by intact bridging regions of the sub-web, wherein the interrupted slits are nonlinear and extend predominantly in the first direction.

In a seventh embodiment, the present disclosure provides the method of the sixth embodiment, wherein at least some of the intact bridging regions of adjacent interrupted slits are offset in the first direction.

In an eighth embodiment, the present disclosure provides the method of the sixth or seventh embodiment, wherein each of the interrupted slits has a wave shape.

In a ninth embodiment, the present disclosure provides the method of any one of the sixth to eighth embodiments, wherein before severing the thermoplastic web, the method further comprises spreading each of the two sub-webs in the second direction to provide two connected spread mechanical fastening strips, wherein the two, connected spread mechanical fastening strips each comprise multiple strands attached to each other at least at some of the intact bridging regions and separated from each other between at least some of the intact bridging regions.

In a tenth embodiment, the present disclosure provides the method of the ninth embodiment, wherein spreading is carried out by moving the two sub-webs over a crowned surface, a bowed roller, diverging disks, or a stretching surface.

In an eleventh embodiment, the present disclosure provides the method of any one of the first to tenth embodiments, wherein spreading is carried out by moving the two sub-webs over a crowned surface, and wherein the crowned surface is stationary.

In a twelfth embodiment, the present disclosure provides the method of any one of the first to eleventh embodiments, wherein spreading is carried out by moving the two sub-webs over a crowned surface, and wherein the crowned surface and the slit web are not moving at the same speed in the same direction.

In a thirteenth embodiment, the present disclosure provides the method of any one of the tenth to twelfth embodiments, wherein at least a portion of the crowned surface is a low-friction surface.

In a fourteenth embodiment, the present disclosure provides the method of any one of the ninth to twelfth embodiments, further comprising heating the two, connected spread mechanical fastening strips, for example, to anneal the two, connected spread mechanical fastening strips.

In a fifteenth embodiment, the present disclosure provides the method of the fourteenth embodiment, wherein heating comprises directing the two, connected spread mechanical fastening strips onto a rotating heated cylinder.

In a sixteenth embodiment, the present disclosure provides the method of the fifteenth embodiment, wherein heating comprises using non-contact heating.

In a seventeenth embodiment, the present disclosure provides the method of any one of the sixth to sixteenth embodiments, further comprising slitting the thermoplastic web to provide the plurality of laterally separated interrupted slits.

In an eighteenth embodiment, the present disclosure provides the method of any one of the first to seventeenth embodiments, wherein the two sub-webs are spread such that the width of the two, connected spread mechanical fastening strips is up to 100 percent greater than the width of the two sub-webs before spreading.

In a nineteenth embodiment, the present disclosure provides the method of any one of the first to eighteenth embodiments, wherein there are at least two nonlinear lines of weakness demarcating nonlinear edges of at least three sub-webs of the thermoplastic web without severing the web.

In a twentieth embodiment, the present disclosure provides the method of any one of the first to nineteenth embodiments, wherein severing the web comprises contacting at least a portion of the nonlinear line of weakness with at least one of a wire, shim, fin, blade, or a machine finger.

In a twenty-first embodiment, the present disclosure provides the method of any one of the first to fourth embodiments, wherein severing the web comprises moving the two sub-webs over a crowned surface, a bowed roller, diverging disks, or a stretching surface.

In a twenty-second embodiment, the present disclosure provides the method of any one of the first to twenty-first embodiments, further comprising applying tension to the web in the first direction.

In a twenty-third embodiment, the present disclosure provides the method of any one of the first to twenty-second embodiments, further comprising forming the nonlinear line of weakness in the thermoplastic web.

In a twenty-fourth embodiment, the present disclosure provides the method of any one of the first to twenty-third embodiments, wherein providing the thermoplastic web comprises unwinding the thermoplastic web from a roll.

In a twenty-fifth embodiment, the present disclosure provides the method of any one of the first to twenty-fourth embodiments, further comprising directing the two sub-webs onto a high-friction roller after severing the thermoplastic web and before joining the two sub-webs to a carrier.

In a twenty-sixth embodiment, the present disclosure provides the method of the twenty-fifth embodiment, wherein the high-friction roller is heated.

In a twenty-seventh embodiment, the present disclosure provides the method of the twenty-fifth embodiment, wherein the high-friction roller is chilled.

In a twenty-eighth embodiment, the present disclosure provides the method of any one of the first to twenty-seventh embodiments, wherein the first direction is the machine direction.

In a twenty-ninth embodiment, the present disclosure provides the method of any one of the first to twenty-sixth embodiments, wherein joining the two sub-webs to a carrier comprises at least one of adhesive bonding or thermal bonding.

In a thirtieth embodiment, the present disclosure provides the method of any one of the first to twenty-ninth embodiments, wherein the carrier is a nonwoven web.

In a thirty-first embodiment, the present disclosure provides the method of the twenty-ninth or thirtieth embodiments, wherein the carrier is provided with a layer of an adhesive.

In a thirty-second embodiment, the present disclosure provides the method of the twenty-ninth embodiment, wherein the two sub-webs are joined to the carrier with the adhesive, and wherein the adhesive is exposed in a separation between the two sub-webs.

In a thirty-third embodiment, the present disclosure provides the method of the twenty-ninth embodiment, wherein joining the two sub-webs to the carrier comprises:

impinging a heated fluid onto at least one of the second surface of the two sub-webs or a first surface of the carrier; and contacting the second surface of the two sub-webs with the first surface of the carrier so that the second surface of the two sub-webs and the first surface of the carrier melt-bond to each other.

In a thirty-fourth embodiment, the present disclosure provides the method of the thirty-third embodiment, wherein the heated fluid is impinged on the second surface of the two sub-webs.

In a thirty-fifth embodiment, the present disclosure provides the method of the thirty-fourth embodiment, further comprising moving the carrier through ambient-temperature quiescent air.

In a thirty-sixth embodiment, the present disclosure provides the method of any one of the thirty-third to thirty-fifth embodiments, wherein the heated fluid is heated air.

In a thirty-seventh embodiment, the present disclosure provides the method of any one of the first to thirty-sixth embodiments, wherein the mechanical fastening elements are male fastening elements comprising upstanding posts having bases attached to the thermoplastic web.

In a thirty-eighth embodiment, the present disclosure provides the method of the thirty-seventh embodiment, wherein the male fastening elements also comprise caps distal from the thermoplastic web.

In a thirty-ninth embodiment, the present disclosure provides the method of any one of the first to thirty-sixth embodiments, wherein the mechanical fastening elements comprise loops.

This disclosure is not limited to the above-described embodiments but is to be controlled by the limitations set forth in the following claims and any equivalents thereof. This disclosure may be suitably practiced in the absence of any element not specifically disclosed herein.

What is claimed is:

1. A method of making a laminate, the method comprising:
   providing a thermoplastic web having mechanical fastening elements and a nonlinear line of weakness, wherein the nonlinear line of weakness extends predominantly in a first direction and demarcates nonlinear edges of two sub-webs but does not sever the thermoplastic web;
   severing the thermoplastic web at the nonlinear line of weakness into the two sub-webs; and
   joining the two sub-webs to a carrier to form the laminate, wherein the two sub-webs are separated in a second direction perpendicular to the first direction, and wherein severing the thermoplastic web and joining the two sub-webs to the carrier are carried out in-line without offsetting the two sub-webs in the first direction.

2. The method of claim 1, wherein the nonlinear line of weakness has a wave shape.

3. The method of claim 1, wherein the thermoplastic web has two opposing nonlinear longitudinal outer edges.

4. The method of claim 1, wherein the nonlinear line of weakness comprises at least one of a series of perforations or a partial-depth cut.

5. The method of claim 1, wherein each of the two sub-webs comprises a plurality of laterally separated interrupted slits that are interrupted by intact bridging regions of the sub-webs, wherein the interrupted slits are nonlinear and extend predominantly in the first direction.

6. The method of claim 5, wherein each of the interrupted slits has a wave shape.

7. The method of claim 5, wherein before severing the thermoplastic web, the method further comprises spreading each of the two sub-webs in the second direction to provide two connected spread mechanical fastening strips, wherein the two connected spread mechanical fastening strips each comprise multiple strands attached to each other at least at some of the intact bridging regions and separated from each other between at least some of the intact bridging regions.

8. The method of claim 7, wherein spreading is carried out by moving the two sub-webs over a crowned surface, a bowed roller, diverging disks, or a stretching surface.

9. The method of claim 5, further comprising slitting the thermoplastic web to provide the plurality of laterally separated interrupted slits.

10. The method of claim 1, wherein there are at least two nonlinear lines of weakness demarcating nonlinear edges of at least three sub-webs of the thermoplastic web without severing the thermoplastic web.

11. The method of claim 1, wherein severing the thermoplastic web comprises contacting at least a portion of the nonlinear line of weakness with at least one of a wire, shim, fin, blade, or a machine finger.

12. The method of claim 1, further comprising forming the nonlinear line of weakness in the thermoplastic web.

13. The method of claim 1, wherein providing the thermoplastic web comprises unwinding the thermoplastic web from a roll.

14. The method of claim 1, wherein joining the two sub-webs to a carrier comprises at least one of adhesive bonding or thermal bonding.

15. The method of claim 1, further comprising directing the two sub-webs onto a high-friction roller after severing the thermoplastic web and before joining the two sub-webs to the carrier.

16. The method of claim 7, further comprising heating the two, connected spread mechanical fastening strips.

17. The method of claim 1, wherein the first direction is the machine direction.

18. The method of claim 1, wherein the carrier is a nonwoven web.

19. The method of claim 1, wherein the carrier is provided with a layer of an adhesive.

20. The method of claim 1, wherein the mechanical fastening elements are male fastening elements comprising upstanding posts having bases attached to the thermoplastic web.

* * * * *